United States Patent
Abu-Izza et al.

(10) Patent No.: US 10,682,317 B2
(45) Date of Patent: Jun. 16, 2020

(54) KETOGENIC DIET COMPATIBLE FENFLURAMINE FORMULATION

(71) Applicant: ZOGENIX INTERNATIONAL LIMITED, Berkshire (GB)

(72) Inventors: Khawla Abu-Izza, Berkeley, CA (US); David Hickman, Newark (GB); Glenn Morrison, Half Moon Bay, CA (US); Brooks M. Boyd, Berkeley, CA (US)

(73) Assignee: ZOGENIX INTERNATIONAL LIMITED, Berkshire (GB)

( * ) Notice: Subject to any disclaimer, the term of this patent is extended or adjusted under 35 U.S.C. 154(b) by 0 days.

(21) Appl. No.: 16/140,120

(22) Filed: Sep. 24, 2018

(65) Prior Publication Data
US 2019/0091178 A1     Mar. 28, 2019

Related U.S. Application Data

(60) Provisional application No. 62/696,801, filed on Jul. 11, 2018, provisional application No. 62/669,833, filed on May 10, 2018, provisional application No. 62/627,329, filed on Feb. 7, 2018, provisional application No. 62/593,029, filed on Nov. 30, 2017, provisional application No. 62/582,173, filed on Nov. 6, 2017, provisional application No. 62/579,450, filed on Oct. 31, 2017, provisional application No. 62/564,225, filed on Sep. 27, 2017, provisional application No. 62/563,255, filed on Sep. 26, 2017.

(51) Int. Cl.
| | |
|---|---|
| A61K 31/137 | (2006.01) |
| A23L 33/10 | (2016.01) |
| A61P 25/08 | (2006.01) |
| A61K 9/08 | (2006.01) |
| A61K 47/26 | (2006.01) |
| A61K 47/14 | (2017.01) |
| A61K 47/12 | (2006.01) |
| A23L 33/00 | (2016.01) |
| A61K 47/38 | (2006.01) |

(52) U.S. Cl.
CPC ............ *A61K 31/137* (2013.01); *A23L 33/10* (2016.08); *A23L 33/30* (2016.08); *A61K 9/08* (2013.01); *A61K 47/12* (2013.01); *A61K 47/14* (2013.01); *A61K 47/26* (2013.01); *A61K 47/38* (2013.01); *A61P 25/08* (2018.01); *A23V 2002/00* (2013.01); *A23V 2200/3322* (2013.01)

(58) Field of Classification Search
CPC ......... A61K 31/137; A61K 9/08; A61P 25/08; A23L 33/10; A23L 33/30
See application file for complete search history.

(56) References Cited

U.S. PATENT DOCUMENTS

| | | | |
|---|---|---|---|
| 4,452,815 A | 6/1984 | Wurtman | |
| 5,834,477 A | 11/1998 | Mioduszewski | |
| 5,985,880 A | 11/1999 | Chang | |
| 6,599,901 B1 | 7/2003 | Flohr | |
| 9,125,900 B2 | 9/2015 | Meyer | |
| 9,549,909 B2 | 1/2017 | Ceulemens | |
| 9,603,814 B2 | 3/2017 | Ceulemens | |
| 9,603,815 B2 | 3/2017 | Ceulemens | |
| 9,610,260 B2 | 4/2017 | Ceulemens | |
| 2003/0118654 A1* | 6/2003 | Santos | A61K 9/0095 424/486 |
| 2005/0182103 A1 | 8/2005 | Finke et al. | |
| 2006/0121066 A1 | 6/2006 | Jaeger et al. | |
| 2006/0270611 A1 | 11/2006 | Dries et al. | |
| 2008/0261962 A1 | 10/2008 | Greer | |
| 2010/0298181 A1 | 11/2010 | Hanada et al. | |
| 2011/0092535 A1 | 4/2011 | Barnes et al. | |
| 2011/0212171 A1 | 9/2011 | Venkatesh et al. | |
| 2012/0115958 A1* | 5/2012 | Mariotti | A61K 9/0095 514/629 |
| 2012/0270848 A1 | 10/2012 | Mannion | |
| 2013/0296398 A1 | 11/2013 | Whalley | |
| 2014/0030343 A1 | 1/2014 | Lamson | |
| 2014/0162942 A1 | 6/2014 | Ghosal | |
| 2014/0329908 A1 | 11/2014 | Ceulemens et al. | |
| 2014/0343162 A1 | 11/2014 | Ceulemens et al. | |
| 2015/0080377 A1 | 3/2015 | Dhanoa | |
| 2015/0291597 A1 | 10/2015 | Mannion | |
| 2015/0359755 A1 | 12/2015 | Guy et al. | |
| 2016/0136114 A1 | 5/2016 | Ceulemens et al. | |

(Continued)

FOREIGN PATENT DOCUMENTS

| | | |
|---|---|---|
| JP | H05-310564 A | 11/1993 |
| WO | WO 2005/004865 | 1/2005 |

(Continued)

OTHER PUBLICATIONS

Wallace et al., "Pharmacotherapy for Dravet Syndrome," Paediatr. Drugs Jun. 2016;18(3):197-208. PMID: 26966048. (Year: 2016).*

(Continued)

*Primary Examiner* — Theodore R. West
(74) *Attorney, Agent, or Firm* — Karl Bozicevic; Bozicevic Field & Francis LLP

(57) ABSTRACT

A method of treating symptoms of a subtype of epilepsy, e.g., Dravet syndrome, in a patient diagnosed with a subtype of epilepsy, by administering to the patient an effective dose of a fenfluramine formulation in combination with a ketogenic diet over a period of time sufficient to reduce or completely eliminate seizures in the patient. Also provided are compositions and kits finding use in practicing embodiments of the methods.

11 Claims, No Drawings

(56) References Cited

U.S. PATENT DOCUMENTS

| | | |
|---|---|---|
| 2017/0020885 A1 | 1/2017 | Hsu |
| 2017/0056344 A1 | 3/2017 | Farr et al. |
| 2017/0071949 A1 | 3/2017 | De Witte et al. |
| 2017/0174613 A1 | 6/2017 | Londesbrough et al. |
| 2017/0348303 A1 | 12/2017 | Bosse |
| 2018/0028499 A1 | 2/2018 | Baraban et al. |
| 2018/0092864 A1 | 4/2018 | Martin et al. |
| 2018/0141953 A1 | 5/2018 | Dax |
| 2018/0148403 A1 | 5/2018 | Londesbrough et al. |
| 2018/0215701 A1 | 8/2018 | Carroll et al. |

FOREIGN PATENT DOCUMENTS

| | | |
|---|---|---|
| WO | WO 2008/025148 | 3/2008 |
| WO | WO 2010/020585 | 2/2010 |
| WO | WO 2014/177676 | 11/2014 |
| WO | WO 2015/026849 | 2/2015 |
| WO | WO 2015/066344 | 5/2015 |
| WO | WO 2015/193668 | 12/2015 |
| WO | WO 2016/138138 | 9/2016 |
| WO | WO 2017-035267 | 3/2017 |
| WO | WO 2018/037306 | 3/2018 |
| WO | WO 2018/060732 | 4/2018 |
| WO | WO 2018/206924 | 11/2018 |

OTHER PUBLICATIONS

Wirrell, "Treatment of Dravet Syndrome," Can. J. Neurol. Sci. Jun. 2016;43 Suppl 3:S13-18. PMID: 27264138. (Year: 2016).*

Anonymous, "Determination That PONDIMIN (Fenfluramine Hydrochloride) Tablets, 20 Milligrams and 60 Milligrams, and PONDEREX (Fenfluramine Hydrochloride) Capsules, 20 Milligrams Were Withdrawn From Sale for Reasons of Safety or Effectiveness", Federal Register, (Sep. 29, 2015).

Brunklaus et al., "Dravet syndrome-From epileptic encephalopathy to channelopathy" Epilepsia (May 16, 2014) 55(7):979-984.

Buchanan, Gordon F. et al., Serotonin neurones have anticonvulsant effects and reduce seizure-induced mortality, The Journal of Physiology, 2014, vol. 592, Issue 19, p. 4395-4410.

C. B. Catarino et al. "Dravet Syndrome as epileptic encephalopathy: Evidence from long-term course and neuropathology", Brain, vol. 134, No. 10 (Jun. 29, 2011) pp. 2982-3010.

Ceulemans et al., "Poster presented at the 69th Annual Meeting of the American Epilepsy Society" (Dec. 2015) Philadelphia.

Devinsky et al., "Trial of Cannabidiol for Drug-Resistant Seizures in the Dravet Syndrome" The New Engalnd Journal of Medicine (May 25, 2017) 376(21):2011-2020.

Döring et al. "Thirty Years of Orphan Drug Legislation and the Development of Drugs to Treat Rare Seizure Conditions: A Cross Sectional Analysis" PLOS One, pp. 1-15 (Aug. 24, 2016).

Gastaut et al., "Compulsive respiratory sterotypies in children with autistic features: Polygraphic recording and treatment with fenfluramine" Journal of Autism and Developmental Disorders, (Sep. 1, 1987) 17(3):391-406.

Gioia et al., "Confirmatory Factor Analysis of the Behavior Rating Inventory of Executive Function (BRIEF) in a Clinical Sample" Child Neuropsychology (2002) 8(4):249-57.

Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.

Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.

Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.

LeJeune et al, "Psychometric Support for an Abbreviated Version of the Behavior Rating Inventory of Executive Function (BRIEF) Parent Form" Child Neuropsychology (2010 16:182-201.

Martin, et al., "An Examination of the Mechanism of Action of Fenfluramine in Dravet Syndrome: A Look Beyond Serotonin" Presented as part of the Zogenix Scientific Exhibit During the 70th Annual Meeting of the American Epilepsy Society, Houston, Texas (Dec. 2-6, 2016).

NCT02682927 (Sep. 3, 2016, 10 pages) Accessed from https://www.clinicaltrials.gov/ct2/history/NCT02682927?V=View#StudyPageTop on Mar. 18, 2019).

Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.

Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.

Viola et al., "The Behavior Rating Inventory of Executive Function (BRIEF) to Identify Pediatric Acute Lymphoblastic Leukemia (ALL) Survivors At Risk for Neurocognitive Impairment" Journal of Pediatric Hematology/Oncology (Apr. 1, 2017) 39(3):174-178.

Wirrell et al., "Optimizing the Diagnosis and Management of Dravet Syndrome: Recommendations From a North American Consensus Panel" Pediatric Neurology (Mar. 2017) 68:18-34.

Wurtman et al., "Fenfluramine and other serotoninergic drugs depress food intake and carbohydrate consumption while sparing protein consumption" Current Medical Research and Opinion (1979) 6(1 Supp):28-33.

Anandam, R., Affiliations Indian Journal of Pediatrics (Jan. 1, 2000) 67 (1 Suppl):S88-91 (Abstract Only).

Anonymous, "Determination That PONDIMIN (Fenfluramine Hydrochloride) Tablets, 20 Milligrams and 60 Milligrams, and PONDEREX (Fenfluramine Hydrochloride) Capsules, 20 Milligrams Were Withdrawn From Sale for Reasons of Safety or Effectiveness".

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Arzimanoglou, "Dravet syndrome: From electroclinical characteristics to molecular biology" Epilepsia, 50(Suppl. 8):3-9 (2009).

Boel and Casaer et al., "Add-on Therapy of Fenfluramine in Intractable Self-Induced Epilepsy" Neuropaediatrics 1996, 27(4):171-173.

Brunklaus et al., "Prognostic, clinical and demographic features in SCN1A mutation-positive Dravet syndrome" BRAIN, 2012, p. 1-8.

Carvalho et al., "d-Amphetamine Interaction with Glutathione in Freshly Isolated Rat Hepatocytes" Chemical Research in Toxicology (Jan. 1996) 9(6):1031-1036.

Casaer et al., "Fenfluramine as a Potential Antiepileptic Drug" Epilepsia, 43(2), 205-206, 2002.

C. Doege et al., "Myoclonic-astatic epilepsy: Doose-Syndrum 2014: Doose syndrome 2014", Zeitschrift FR Epileptologie, (Mar. 20, 2014).

Ceulemans et al., "Successful use of fenfluramine as an add-on treatment for Dravet syndrome" Epilepsia, 53(7), 2012, 1131-1139.

Ceulemans, "Overall management of patients with Dravet syndrome" Developmental Medicine & Child Neurology, 2011, 53, 19-23.

Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).

Ceulemans B., "Successful Use of Fenfluramine as Add-On Treatment in Dravet Syndrome" Epilepsia, 52(Suppl. 6):4-22 (2011).

Ceulemans et al., "Five-year extended follow-up status of 10 patients with Dravet syndrome treated with fenfluramine" Epilepsia (May 20, 2016) 57(7):e129-e134.

Chiron et. al., "The pharmacologic treatment of Dravet syndrome" Epilepsia (2011) 52(Suppl 2):72-75.

Clemens B., "Dopamine agonist treatment of self-induced pattern-sensitive epilepsy. A case Report" Epilepsy Res. 2. 1988, p. 340-343.

(56) References Cited

OTHER PUBLICATIONS

Curzon et al., "Appetite suppression by commonly used drugs depends on 5-HT receptors but not on 5-HT availability" TIPS (1997) 18:21-25.

Franco-Perez, Javier "The Selective Serotonin Reuptake Inhibitors: Antidepressants with Anticonvulsant Effects?" Ann Deoress Anxiety (2014) 1(5):1025 (2 pages).

K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 41(8):925-928.

Gharedaghi et al., "The role of different serotonin receptor subtypes in seizure susceptibility" Exp. Brain Res (2014) 232:347-367.

Habibi et al., "The Impact of Psychoactive Drugs on Seizures and Antiepileptic Drugs" Current Neurology and Neuroscience Reports (Jun. 17, 2016) 16(8):1-10.

Haritos et al., "Metabolism of dexfenfluramine in human liver microsomes and by recombinant enzymes: Role of CYP2D6 and 1A2" Pharmcogenetics (Oct. 1998) 8(5):423-432.

Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . . ).

Hazai et al., "Reduction of toxic metabolite formation of acetaminophen" Biochemical and Biophysical Research Communications (Mar. 8, 2002) 291(4):1089-1094.

Hegadoren et al., "Interactions of iprindole with fenfluramine metabolism in rat brain and liver" Journal of Psychiatry & Neuroscience (Mar. 1991) pp. 5-11.

Katholieke Universiteit Leuven, University Hospital Antwerp: "Interim results of a fenfluramine open-label extension study", European Patent Register (May 25, 2017).

Lagae et al. "A pilot, open-label study of the effectiveness and tolerability of low-dose ZX008 (fenfluramine HC1) in Lennox-Gastaut syndrome" Epilepsia (2018) 59: 1881-1888.

Lopez-Meraz et al., "5-$HT_{1A}$ receptor agonist modify epileptic seizures in three experimental models in rats" Neuropharmacology (2005) 49:367-375.

Martin, et al., "An Examination of the Mechanism of Action of Fenfluramine in Dravet Syndrome: A Look Beyond Serotonin" Presented as part of the Zogenix Scientific Exhibit During the 70th Annual Meeting of the American Epilepsy Society, Houston, Texas.

Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.

Mudigoudar et al., "Emerging Antiepileptic Drugs for Severe Pediatric Epilepsies" Seminars in Pediatric Neurology (Jun. 2016) 23(2):167-179.

Mulley et al., "SCN1A Mutations and Epilepsy" Human Mutation (2005) 25:535-542.

Naithani et al., "The Conventional Antiepileptic Drug Use When Compared to a Combination Therapy Regime in a Teaching Hospital in India" International Journal of Pharma and Bio Sciences (2012) 3(1):B-191-B-197.

Nozulak et al., "(+)-cis-4,5,7a,8,9,10,11,11a-Octahydro-7H-10-methylindolo[1,7-bc][2,6]-naphthridine: A 5-$HT_{2C/2B}$ Receptor Antagonist with Low 5-$HT_{2A}$ Receptor Affinity" J. Med. Chem. (1995) 38:28-33.

O'Neill et al., "GR46611 potentiates 5-$HT_{1A}$ receptor-mediated locomotor activity in the guinea pig" European Journal of Pharmacology (1999) 370:85-92.

Pirincci et al., "The Effects of Fenfluramine on Blood and Tissue Seratonin (5-Hydroxytryptamine) Levels in Rats" Turk J Vet Anim Sci (2005) 29:857-863.

Remington, "The Science and Practice of Pharmacy", Nineteenth Edition (1995), pp. 710-712.

Rho, Jong M. "Basic Science Behind the Catastrophic Epilepsies" Epilepsia (2004) 45(Suppl. 5):5-11.

Rothman et al., "Serotonergic drugs and valvular heart disease" Expert Opinion on Drug Safety (May 2009) 8(3):317-329.

Schoonjans, An-Sofie "Low-dose fenfluramine in the treatment of neurologic disorders: experience in Dravet syndrome" Therapeutic Advances in Neurological Disorders (Jan. 1, 2015) pp. 328-338.

Sourbron et al., "Serotonergic Modulation as Effective Treatment for Dravet Syndrome in Zebrafish Mutant Model" ACS Chemical Neuroscience (Feb. 17, 2016) 7(5):588-598.

Sharma et al. Indian Journal of Pharmacology, 1996, 28(1), 1-10.

Sullivan et al. "Effect of ZX008 (fenfluramine HC1 oral solution) on total seizures in Dravet syndrome" Neurology: Official Journal of the American Academy of Neurology, 2018, 90(24):e2187-e2811.

Vickers et al., "Oral Administration of the 5-HT2C receptor agonist, mCPP, reduces body weight gain in rats over 28 days as a result of maintained hypophagia" Psychopharmacology (May 2003), 167 (3): 274-280.

Wirrell et al., "Stiripentol in Dravet syndrome: Results of a retrospective U.S. study" Epilepsia (2013) 54(9):1595-1604.

Yamaori et al., "Potent inhibition of human cytochrome P450 3A isoforms by cannabidiol: Role of phenolic hydroxyl groups in the resorcinol moiety" Life Sciences (2011) 88:730-736.

Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.

Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS)*. Presented at the 2016.

Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts.

Zhuang et al. (2016), "PBPK modeling and simulation in drug research and development" in Acta Pharmaceutica Sinica B 2016;6(5):430-440.

ZOGENIX "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].

Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).

F Brenot et al., "Primary Pulmonary Hypertension and Fenfluramine Use.", HEART, vol. 70, No. 6, Dec. 1, 1993 (Dec. 1, 1993), pp. 537-541.

Favale et al., "The anticonvulsant effect of citalopram as indirect evidence of serotonergic impairment in human epileptogenesis" Seizure (2003) 12:316-319.

Jake Remaly: "Fenfluramine Reduces Convulsive Seizure Frequency in Dravet Syndrome. Epilepsy Resource Center", Jan. 1, 2018 (Jan. 1, 2018).

An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.

Faingold et al., "Prevention of seizure-induced sudden death in a chronic SUDEP model by semichronic administration of a selective serotonin reuptake inhibitor" Epilepsy & Behavior (2011) 22:186-190.

Manzke et al., "5-HT4(a) receptors avert opiod-induced breathing depression without loss of analgesia" Science (Jul. 11, 2003) 301:226-229.

Wirrell et al., "Stiripentol in Dravet Syndrome: Is it Worth It?" Epilepsy Currents, 14(1):22-23 (Jan./Feb. 2014).

* cited by examiner

KETOGENIC DIET COMPATIBLE FENFLURAMINE FORMULATION

FIELD OF THE INVENTION

A method of treating patients with a subtype of epilepsy (e.g., Dravet syndrome, Lennox-Gastaut syndrome, Doose syndrome), is described whereby the patient is treated with a fenfluramine formulation in combination with a ketogenic diet.

BACKGROUND OF THE INVENTION

This invention relates to the treatment of a subtype of epilepsy (e.g., Dravet syndrome, Lennox-Gastaut syndrome, Doose syndrome) using an amphetamine derivative, specifically fenfluramine.

Fenfluramine, i.e., 3-trifluoromethyl-N-ethylamphetamine, is an amphetamine derivative having the structure:

Structure 1

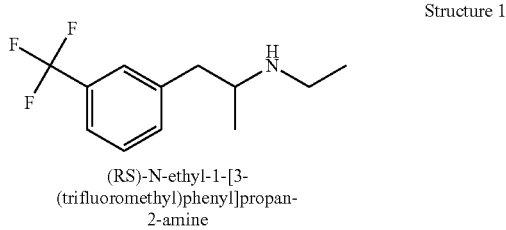 [SMILES: CCNC(C)Cc1cccc(C(F)(F)F)c1]

(RS)-N-ethyl-1-[3-(trifluoromethyl)phenyl]propan-2-amine

Fenfluramine was first marketed in the US in 1973 and had been administered in combination with phentermine to prevent and treat obesity. However, in 1997, it was withdrawn from the US market as its use was associated with the onset of cardiac fibrosis and pulmonary hypertension. Subsequently, the drug was withdrawn from sale globally and is no longer indicated for use in any therapeutic area.

Despite the health concerns surrounding fenfluramine, attempts have been made to identify further therapeutic uses for that product. Aicardi and Gastaut (*New England Journal of Medicine* (1985), 313:1419 and *Archives of Neurology* (1988) 45:923-925) reported four cases of self-induced photosensitive seizures that responded to treatment with fenfluramine.

Clemens, in *Epilepsy Research* (1988) 2:340-343 reported a study on a boy suffering pattern sensitivity-induced seizures that were resistant to anticonvulsive treatment. Fenfluramine reportedly successfully terminated these self-induced seizures and the author concluded that this was because fenfluramine blocked the photosensitive triggering mechanism.

In *Neuropaediatrics*, (1996); 27(4):171-173, Boel and Casaer reported on a study on the effects of fenfluramine on children with refractory epilepsy. They concluded that when fenfluramine was administered at a dose of 0.5 to 1 mg/kg/day, this resulted in a reduction in the number of seizures experienced by the patients.

In a letter to *Epilepsia*, published in that journal (*Epilepsia*, 43(2):205-206, 2002), Boel and Casaer commented that fenfluramine appeared to be of therapeutic benefit in patients with intractable epilepsy.

Epilepsy is a condition of the brain marked by a susceptibility to recurrent seizures. There are numerous causes of epilepsy including, but not limited to birth trauma, perinatal infection, anoxia, infectious diseases, ingestion of toxins, tumors of the brain, inherited disorders or degenerative disease, head injury or trauma, metabolic disorders, cerebrovascular accident and alcohol withdrawal.

There are a large number of subtypes of epilepsy that have been characterized. For example, the most recent classification system adopted by the International League Against Epilepsy's ("ILAE") Commission on Classification and Terminology provides the following list of epilepsy syndromes (See Berg et. al., "Revised terminology and concepts for organization of seizures," *Epilepsia*, 51(4):676-685 (2010)):

I. Electroclinical syndromes arranged by age at onset:

A. Neonatal period (1. Benign familial neonatal epilepsy (BFNE), 2. Early myoclonic encephalopathy (EME), 3. Ohtahara syndrome), B. Infancy (1. Epilepsy of infancy with migrating focal seizures, 2. West syndrome, 3. Myoclonic epilepsy in infancy (MEI), 4. Benign infantile epilepsy, 5. Benign familial infantile epilepsy, 6. Dravet syndrome, 7. Myoclonic encephalopathy in nonprogressive disorders), C. Childhood (1. Febrile seizures plus (FS+) (can start in infancy), 2. Panayiotopoulos syndrome, 3. Epilepsy with myoclonic atonic (previously astatic) seizures, 4. Benign epilepsy with centrotemporal spikes (BECTS), 5. Autosomal-dominant nocturnal frontal lobe epilepsy (ADNFLE), 6. Late onset childhood occipital epilepsy (Gastaut type), 7. Epilepsy with myoclonic absences, 8. Lennox-Gastaut syndrome, 9. Epileptic encephalopathy with continuous spike-and-wave during sleep (CSWS), 10. Landau-Kleffner syndrome (LKS), 11. Childhood absence epilepsy (CAE));

D. Adolescence—Adult (1. Juvenile absence epilepsy (JAE), 2. Juvenile myoclonic epilepsy (JME), 3 Epilepsy with generalized tonic—clonic seizures alone, 4. Progressive myoclonus epilepsies (PME), 5. Autosomal dominant epilepsy with auditory features (ADEAF), 6. Other familial temporal lobe epilepsies, E. Less specific age relationship (1 Familial focal epilepsy with variable foci (childhood to adult), 2. Reflex epilepsies);

II. Distinctive constellations: A. Mesial temporal lobe epilepsy with hippocampal sclerosis (MTLE with HS), B. Rasmussen syndrome, C. Gelastic seizures with hypothalamic hamartoma, D. Hemiconvulsion—hemiplegia—epilepsy, E. Other epilepsies, distinguished by 1. presumed cause (presence or absence of a known structural or metabolic condition, then 2. primary mode of seizure onset (generalized vs. focal);

III. Epilepsies attributed to and organized by structural-metabolic causes: A. Malformations of cortical development (hemimegalencephaly, heterotopias, etc.), B. Neurocutaneous syndromes (tuberous sclerosis complex, Sturge-Weber, etc.), C. Tumor, D. Infection, E. Trauma;

IV. Angioma: A. Perinatal insults, B. Stroke, C. Other causes;

V. Epilepsies of unknown cause;

VI Conditions with epileptic seizures that are traditionally not diagnosed as a form of epilepsy per se; A. Benign neonatal seizures (BNS); and B. Febrile seizures (FS).

See Berg et. al, "Revised terminology and concepts for organization of seizures," *Epilepsia*, 51(4):676-685 (2010))

As can be seen from, for example, Part V of that list, there are still subtypes of epilepsy that have not yet been fully characterized and thus, the list is far from complete.

Those skilled in the art will recognize that these subtypes of epilepsy are triggered by different stimuli, are controlled by different biological pathways and have different causes, whether genetic or environmental. In other words, the skilled artisan will recognize that teachings relating to one epileptic subtype are not necessarily applicable to other subtypes. This can include recognition that different epilepsy subtypes respond differently to different anticonvulsant drugs.

Dravet syndrome is a rare and catastrophic form of intractable epilepsy that begins in infancy. Initially, the patient experiences prolonged seizures. In their second year, additional types of seizure begin to occur and this typically coincides with a developmental decline, possibly due to repeated cerebral hypoxia. This leads to poor development of language and motor skills.

Children with Dravet syndrome are likely to experience multiple seizures per day. Epileptic seizures are far more likely to result in death in sufferers of Dravet syndrome; approximately 10 to 15% of patients diagnosed with Dravet syndrome die in childhood, particularly between two and four years of age. Additionally, patients are at risk of numerous associated conditions including orthopedic developmental issues, impaired growth and chronic infections.

Of particular concern, children with Dravet syndrome are particularly susceptible to episodes of Status epilepticus. This severe and intractable condition is categorized as a medical emergency requiring immediate medical intervention, typically involving hospitalization. Status epilepticus can be fatal. It can also be associated with cerebral hypoxia, possibly leading to damage to brain tissue. Frequent hospitalizations of children with Dravet syndrome are clearly distressing, not only to the patient but also to family and caregivers. The ketogenic diet has been associated with reduction in occurrence and severity of status epilepticus, including refractory status epilepticus and is used as a second or third line adjunctive treatment (Williams, T. et al. *Clinical Neurophysiology Practice*, Volume 2, 154-160 (2017).

The cost of care for patients with epilepsy, such as Dravet syndrome, is also high as the affected children require constant supervision and many require institutionalization as they reach teenage years.

At present, although a number of anticonvulsant therapies can be used to reduce the instance of seizures in patients with Dravet syndrome, the results obtained with such therapies are typically poor and those therapies only effect partial cessation of seizures at best. Seizures associated with Dravet syndrome are typically resistant to conventional treatments. Further, many anticonvulsants such as clobazam and clonazepam have undesirable side effects, which are particularly acute in pediatric patients.

Stiripentol is approved in Europe, Canada and Australia and has only recently been approved for marketing in the US, for the treatment of Dravet syndrome. Although it has some anticonvulsant activity on its own as a $GABA_A$ receptor modulator; it acts primarily by inhibiting the metabolism of other anticonvulsants thereby prolonging their activity. It is labeled for use in conjunction with clobazam and valproate. However, concerns remain regarding the use of stiripentol due to its inhibitory effect on hepatic cytochrome P450 enzymes. Further, the interactions of stiripentol with a large number of drugs means that combination therapy (which is typically required for patients with Dravet syndrome) is problematic. Additionally, the effectiveness of stiripentol is limited, with few if any patients ever becoming seizure free.

Polytherapy, the use of two or more anti-epileptic drugs, for the treatment of Dravet syndrome can result in a significant patient burden, as the side effects, or adverse events, from the multiple medications can be additive, and result in limiting the effectiveness of the therapy.

Non-pharmacological treatments of Dravet syndrome have included regulating patient diets. In 1921, the ketogenic diet was utilized to induce the metabolic effects of fasting for the management of seizures (Wilder et al. The effect of ketogenemia on the course of epilepsy. *Mayo Clin. Bull.*, 1921, 2:307-14). As use of antiepileptic drugs grew, the diet became reserved for use in selected patients. However, in recent decades, treatment centers have been adopting the classic ketogenic diet. The diet consists of an intake of three or four times as much fat as carbohydrates and protein combined.

The ketogenic diet has now become an established alternative for managing intractable epilepsy. In a study by Caraballo et al., for example, the diet was administered to subjects with Lennox-Gastaut syndrome (LGS), characterized by high seizure frequency and refractoriness to antiepileptic drugs. After 18 months on the diet, 40% of patients placed on the diet had achieved a more than 50% decrease of seizures. The study concluded that the ketogenic diet, particularly the Johns Hopkins protocol, was an effective and well-tolerated option for patients with LGS (Caraballo et al. Ketogenic diet in patients with Lennox-Gastaut syndrome. *Seizure*, 2014, 23(9):751-5).

Patients who are on a ketogenic diet often have a wide range of carbohydrate caloric intake, and may also be taking several medications. Liquid medications often contain flavoring and sweetening agents which add several grams of carbohydrates to a patient's diet per day. However, the success of the diet depends upon the restriction of carbohydrates to promote ketosis, the metabolic state where ketone bodies in the blood provide energy. The failure to monitor carbohydrate caloric content of medications may disrupt the diet.

There is accordingly a need to provide an improved method for treating or preventing epilepsy (e.g., Dravet syndrome, Lennox-Gastaut syndrome, Doose syndrome) and/or for treating, preventing and/or ameliorating seizures experienced by sufferers of a subtype of epilepsy who are on a ketogenic diet.

SUMMARY OF THE INVENTION

The invention is a method of increasing compliance with a ketogenic diet in a patient diagnosed with a subtype of epilepsy, (e.g., Dravet syndrome, Lennox-Gastaut syndrome, and Doose syndrome) wherein the epilepsy has been refractory to previous treatment regimens, the method comprising administering to a subject a therapeutically effective dose of a formulation of fenfluramine that lacks a nutritive/digestible/glycemic carbohydrate, wherein the formulation decreases the patient's craving for carbohydrates.

In some aspects, described herein is a method of treating a patient with Dravet Syndrome, Lennox-Gastaut syndrome, or Doose syndrome, who starts or maintains a ketogenic diet regimen comprising administering to the patient a fenfluramine formulation that is free of digestible carbohydrates, and the administration reduces the patients craving for carbohydrates, thereby facilitating/promoting adherence to the ketogenic diet.

In an aspect of the invention, the formulation is prepared such that the formulation is compatible with a ketogenic diet for subjects with a subtype of epilepsy, such as Dravet syndrome, Lennox-Gastaut syndrome, or Doose syndrome. In an aspect of the invention, administration of the formulation of fenfluramine improves compliance with the ketogenic diet in a patient with Dravet syndrome or other refractory epilepsy.

In another aspect, herein described is a liquid fenfluramine formulation for the treatment of epilepsy, wherein the formulation contains no digestible carbohydrate, and which reduces carbohydrate craving, thereby promoting adherence to a ketogenic diet.

Also provided are compositions and kits finding use in practicing embodiments of the methods.

DETAILED DESCRIPTION OF THE INVENTION

Before the present methods of treatment are described, it is to be understood that this invention is not limited to particular method described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a step of administering" includes a plurality of such steps and reference to "the symptom" includes reference to one or more symptoms and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Specific Aspects of the Invention

After many years of extensive research, it has unexpectedly been found that fenfluramine can be administered as described here to reduce or eliminate seizures in patients with Dravet syndrome, Lennox-Gastaut syndrome, or Doose syndrome. This is confirmed, for example, in the article by Ceulemans et al., *Epilepsia* (2012) 53(7):1131-1139, the contents of which are incorporated herein.

For the avoidance of doubt, the term "prevention" of seizures means the total or partial prevention (inhibition) of seizures. Ideally, the methods of the present invention result in a total prevention of seizures; indeed, this ideal has been achieved in a number of patients treated by the inventors. However, the invention also encompasses methods in which the instances of seizures are decreased by at least 50%, at least 60%, at least 70%, at least 80% or at least 90%.

It is known that patients with Dravet syndrome commonly experience photosensitive or induced seizures. From teachings in the prior art, e.g. Aicardi and Gastaut (1988) and Boel and Casaer (1996)—both discussed above—it might have been expected that fenfluramine would reduce photosensitive or induced seizures. In some instances, however, it has surprisingly been found that all types of seizures exhibited by patients with Dravet syndrome, that is, seizures in addition to and other than those that are photosensitive or induced, can be suppressed by treatment in accordance with a method of the present invention. Thus, in context of the present invention, the term "seizure" is used to not only encompass photosensitive or induced seizures, but some or all of the other types of seizures experienced by patients with epilepsy.

There are a number of genetic mutations that are indicative of epilepsy subtypes and/or related syndromes, e.g., Dravet syndrome, Lennox-Gastaut syndrome, Doose syndrome and West syndrome, all of which are characterized as refractory (difficult to treat or manage) epilepsies.

There are a large number of subtypes of epilepsy that have been characterised. For example, the following list of conditions is set out in Meritt's Neurology (12th Edition): I. Idiopathic epilepsy syndromes (focal or generalised), A. Benign neonatal convulsions, 1. Familial, 2. Nonfamilial, B. Benign childhood epilepsy, 1. With central-midtemporal spikes, 2. With occipital spikes, C. Childhood/juvenile absence epilepsy, D. Juvenile myoclonic epilepsy (including generalised tonic-clonic seizures on awakening), E. Idiopathic epilepsy, otherwise unspecified. II. Symptomatic epilepsy syndromes (focal or generalised), A. West syndrome (infantile spasms), B. Lennox-Gastaut syndrome, C. Early myoclonic encephalopathy, D. *Epilepsia* partialis continua, 1. Rasmussen syndrome (encephalitic form), 2. Restricted form, E. Acquired epileptic aphasia (Landau-Kleffner syndrome), F. Temporal lobe epilepsy, G. Frontal lobe epilepsy, H. Posttraumatic epilepsy, I. Other symptomatic epilepsy, focal or generalised, not specified. III. Other epilepsy syndromes of uncertain or mixed classification, A. Neonatal seizures, B. Febrile seizures, C. Reflex epilepsy, D.

In one aspect, provided herein is a method of increasing compliance with a ketogenic diet in a patient with refractory epilepsy comprising administering a formulation of fenfluramine that lacks a nutritive/digestible/glycemic carbohydrate, wherein the formulation decreases the patient's craving for carbohydrates In some aspects, provided herein is a method of treating a patient with Dravet Syndrome, Lennox-Gastaut syndrome, or Doose syndrome who starts or maintains a ketogenic diet regimen comprising administering to the patient a formulation of fenfluramine wherein the formulation is free of digestible carbohydrates and the administration reduces the patients craving for carbohydrates, thereby facilitating/promoting adherence to the ketogenic diet.

In another aspect, provided herein is a liquid fenfluramine formulation for the treatment of epilepsy which contains no digestible carbohydrate, and which reduces carbohydrate craving, thereby promoting adherence to a ketogenic diet.

According to a further aspect of the present invention, provided herein is a method of treating a patient that exhibits a mutation in one, some or all of the genes, as described below, by administering to that patient an effective dose of fenfluramine in combination with a ketogenic diet. Mutations may include partial or total deletion mutations, truncating mutations and/or missense mutations. In some embodiments, the patient has been diagnosed with a subtype of epilepsy selected from the group consisting of Dravet syndrome, Lennox-Gastaut syndrome, and Doose syndrome. In certain embodiments of this aspect of the invention, the patient has been diagnosed with Dravet syndrome.

In some instances, the mutations occur in genes that are linked diseases and conditions characterized by various seizure types including, for example, generalized seizures, myoclonic seizures, absence seizures, and febrile seizures. Mutations may occur in one or more of the following genes: ALDH7A1, CACNA1A, CACNA1H, CACNB4, CASR, CHD2, CHRNA2, CHRNA4, CHRNB2, CLCN2, CNTN2, CSTB, DEPDC5, EFHC1, EPM2A, GABRA1, GABRB3, GABRD, GABRG2, GOSR2, GPR98, GRIN1, GRIN2A, GRIN2B, KCNMA1, KCNQ2, KCNQ3, KCTD7, MBD5, ME2, NHLRC1, PCDH19, PRICKLE1, PRICKLE2, PRRT2, SCARB2, SCN1A, SCN1B, SCN2A, SCN4A, SCN9A, SLC2A1, TBC1D24.

In some instances, the mutations occur in genes that are linked to age-related epileptic encephalopathies including, for example, early infantile epileptic encephalopathy. Mutations may occur in one or more of the following genes: ALDH7A1, ARHGEF9, ARX, CDKL5, CNTNAP2, FH, FOXG1, GABRG2, GRIN2A, GRIN2B, KCNT1, MAGI2, MAPK10, MECP2, NRXN1, PCDH19, PLCB1, PNKP, PNPO, PRRT2, RNASEH2A, RNASEH2B, RNASEH2C, SAMHD1, SCN1A, SCN1B, SCN2A, SCN8A, SCN9A, SLC25A22, SLC2A1, SLC9A6, SPTAN1, STXBP1, TCF4, TREX1, UBE3A, ZEB2.

In some instances, the mutations occur in genes that are linked to malformation disorders including, for example, neuronal migration disorders, severe microcephaly, pontocerebellar hypoplasia, Joubert syndrome and related disorders, holoprosencephaly, and disorders of the RAS/MAPK pathway. Mutations may occur in one or more of the following genes: AHI1, ARFGEF2, ARL13B, ARX, ASPM, ATR, BRAF,C12orf57, CASK, CBL, CC2D2A, CDK5RAP2, CDON, CENPJ, CEP152, CEP290, COL18A1, COL4A1, CPT2, DCX, EMX2, EOMES, FGF8, FGFR3, FKRP, FKTN, FLNA, GLI2, GLI3, GPR56, HRAS, INPP5E, KAT6B, KRAS, *LAMA2*, LARGE, MAP2K1, MAP2K2, MCPH1, MED17, NF1, NPHP1, NRAS, OFD1, PAFAH1B1, PAX6, PCNT, PEX7, PNKP, POMGNT1, POMT1, POMT2, PQBP1, PTCH1, PTPN11, RAB3GAP1, RAF1, RARS2, RELN, RPGRIP1L, SHH, SHOC2, SIX3, SLC25A19, SNAP29, SOS1, SPRED1, SRD5A3, SRPX2, STIL, TGIF1, TMEM216, TMEM67, TSEN2, TSEN34, TSEN54, TUBA1A, TUBAE, TUBB2B, VDAC1, WDR62, VRK1, ZIC2.

In some instances, the mutations occur in genes that are linked to epilepsy in X-linked intellectual disability. Mutations may occur in one or more of the following genes: ARHGEF9, ARX, ATP6AP2, ATP7A, ATRX, CASK, CDKL5, CUL4B, DCX, FGD1, GPC3, GRIA3, HSD17B10, IQSEC2, KDM5C, MAGT1, MECP2, OFD1, OPHN1, PAK3, PCDH19, PHF6, PLP1, PQBP1, RAB39B, SLC16A2, SLC9A6, SMC1A, SMS, SRPX2, SYN1, SYP.

In some instances, the mutations occur in genes that are linked to storage diseases and conditions characterized by organelle dysfunction including, for example, neuronal ceroid lipofuscinosis, lysosomal storage disorders, congenital disorders of glycosylation, disorders of peroxisome biogenesis, and leukodystrophies. Mutations may occur in one or more of the following genes: AGA, ALG1, ALG12, ALG2, ALG3, ALG6, ALG8, ALG9, ALG11, ALG13, ARSA, ARSB, ASPA, B4GALT1, CLN3, CLN5, CLN6, CLN8, COG1, COG4, COG5, COG6, COG7, COG5, CTSA, CTSD, DDOST, DOLK, DPAGT1, DPM1, DPM3, EIF2B1, EIF2B2, EIF2B3, EIF2B4, EIF2B5, FUCA1, GALC, GALNS, GFAP, GLB1, GNE, GNPTAB, GNPTG, GNS, GUSB, HEXA, HEXB, HGSNAT, HYAL1, IDS, IDUA, MCOLN1, MFSD8, MGAT2, MLC1, MOGS, MPDU1, MPI, NAGLU, NEU1, NOTCH3, NPC1, NPC2, PEX1, PEX12, PEX14, PEX2, PEX26, PEX3, PEX5, PEX6, PEX7, PEX10, PEX13, PEX16, PEX19, PGM1, PLP1, PMM2, PPT1, PSAP, RFT1, RNASEH2A, RNASEH2B, RNASEH2C, SAMHD1, SDHA, SGSH, SLC17A5, SLC35A1, SLC35A2, SLC35C1, SMPD1, SUMF1, TMEM165, TPP1, TREX1

In some instances, the mutations occur in genes that are linked to syndromic disorders with epilepsy including, for example, juvenile myoclonic epilepsy, childhood absence epilepsy, benign rolandic epilepsy, Lennox-Gastaut syndrome, Dravet syndrome, Ohtahara syndrome, West syndrome, etc. Mutations may occur in one or more of the following genes: ATP2A2, ATP6V0A2, BCKDK, CACNA1A, CACNB4, CCDC88C, DYRK1A, HERC2, KCNA1, KCNJ10, KIAA1279, KMT2D, LBR, LGI1, MAPK10, MECP2, MEF2C, NDE1, NIPBL, PANK2, PIGV, PLA2G6, RAII, RBFOX1, SCN8A, SERPINI1, SETBP1, SLC1A3, SLC4A10, SMC3, SYNGAP1, TBX1, TSC1, TSC2, TUSC3, UBE3A, VPS13A, VPS13B In some instances, the mutations occur in genes that are linked to the occurrence of migraines. Mutations may occur in one or more of the following genes: ATP1A2, CACNA1A, NOTCH3, POLG, SCN1A, SLC2A1.

In some instances, the mutations occur in genes that are linked to Hyperekplexia. Mutations may occur in the following genes: ARHGEF9, GLRA1, GLRB, GPHN, SLC6A5.

In some instances, the mutations occur in genes that are linked to inborn errors of metabolism including, for example, disorders of carbohydrate metabolism, amino acid metabolism disorders, urea cycle disorders, disorders of organic acid metabolism, disorders of fatty acid oxidation and mitochondrial metabolism, disorders of porphyrin metabolism, disorders of purine or pyridine metabolism, disorders of steroid metabolism, disorders of mitochondrial function, disorders of peroxisomal function, and lysosomal storage disorders. Mutations may occur in one or more of the following genes: ABAT, ABCC8, ACOX1, ACY1, ADCK3, ADSL, ALDH4A1, ALDH5A1, ALDH7A1, AMT, ARG1, ATIC, ATP5A1, ATP7A, ATPAF2, BCS1L, BTD, C12ORF65, CABC1, COQ2, COQ9, COX10, COX15, DDC, DHCR7, DLD, DPYD, ETFA, ETFB, ETFDH, FOLR1, GAMT, GATM, GCDH, GCSH, GLDC, GLUD1, GLUL,HPD, HSD17B10, HSD17B4, KCNJ11, L2HGDH, LRPPRC, MGME1, MMACHC, MOCS1, MOCS2, MTHFR, MTR, MTRR, NDUFA1, NDUFA2, NDUFAF6, NDUFS1, NDUFS3, NDUFS4, NDUFS7, NDUFS8, NDUFV1, PC, PDHA1, PDHX, PDSS1, PDSS2, PGK1, PHGDH, POLG, PRODH, PSAT1, QDPR, RARS2, SCO2, SDHA, SLC19A3, SLC25A15, SLC46A1, SLC6A8, SUCLA2, SUOX, SURF1, TACO1, TMEM70, VDAC1.

Fenfluramine has been known to inhibit serotonin reuptake and to trigger the release of serotonin in the brain due to disruption of its vesicular storage. Data from more recent studies provide evidence that fenfluramine is a positive allosteric modulator of the sigma-1 receptor. In the present invention, fenfluramine's mechanism of action made it suitable for the treatment of a subtype of epilepsy, e.g., Dravet syndrome, Lennox-Gastaut syndrome, or Doose syndrome. According to a further aspect of the present invention, there is provided a method of stimulating or modulating one or more targets in the brain of a patient by administering an effective dose of fenfluramine in combination with a ketogenic diet to said patient, wherein said one or more targets are selected from the group consisting of a chaperone protein, a bioamine transporter (BAT), and a 5-HT receptor.

In a method of the present invention, fenfluramine can be employed as a monotherapy in the treatment of a subtype of epilepsy, e.g., Dravet syndrome, Lennox-Gastaut syndrome, or Doose syndrome. Alternatively, fenfluramine can be co-administered simultaneously, sequentially or separately with one or more co-therapeutic agents, such as anticonvulsants. Preferred co-therapeutic agents can be selected from the group consisting of carbamazepine, ethosuximide, fosphenytoin, lamotrigine, levetiracetam, phenobarbital, progabide, topiramate, stiripentol, valproic acid, valproate, verapamil, and benzodiazepines such as clobazam, clonazepam, diazepam, ethyl loflazepate, lorazepam, midazolam. Use of a pharmaceutically acceptable salt of a co-therapeutic agent is also contemplated. However, carbamazepine, oxcarbazepine, lamotrigine, phenytoin and vigabatrin are typically contraindicated in Dravet syndrome, as they tend to make seizures worse, rather than better.

According to aspects of the invention, there is provided a method of treating a subject, e.g., a patient, diagnosed with a subtype of epilepsy (e.g., Dravet syndrome, Lennox-Gastaut syndrome, or Doose syndrome) by administering to the subject a therapeutically effective dose of a fenfluramine active agent. Fenfluramine active agents include fenfluramine or a pharmaceutically acceptable salt or conjugate thereof. As such, fenfluramine can be administered in the form of the free base, or in the form of a pharmaceutically acceptable salt, for example selected from the group consisting of hydrochloride, hydrobromide, hydroiodide, maleate, sulphate, tartrate, acetate, citrate, tosylate, succinate, mesylate and besylate. Further illustrative pharmaceutically acceptable salts can be found in Berge et al., *J. Pharm Sci.* (1977) 68(1):1-19.

Fenfluramine for use in the methods of the present invention may be produced according to any pharmaceutically acceptable process known to those skilled in the art. Examples of processes for synthesizing fenfluramine are provided in the following documents: GB1413070, GB1413078 and EP441160.

In embodiments of the invention, any effective dose of fenfluramine can be employed. In some cases, surprisingly low doses of fenfluramine have been found by the inventors to be efficacious, particularly for inhibiting or eliminating seizures in Dravet syndrome, Lennox-Gastaut syndrome, or Doose syndrome patients. Furthermore, a surprisingly low dose fenfluramine is also effective in reducing appetite and craving for carbohydrates, compared to the dose required for treatment of obesity in adults (usually 60-120 mg/day). Wurtman et al. described a reduction in carbohydrate craving in adults who were treated with 30 mg/day of dexfenfluramine (*Int. J. Eat. Disord.*, 1985, 4:89-99). The overall anorectic effect of dexfenfluramine is greater than that of 1-fenfluramine in experimental animals (Garratini et al. 1988) and humans (Goodall et al. 1992). Dexfenfluramine was found to possess twice the anorectic potency of the racemic mixture fenfluramine when directly compared in a group of 16 human subjects. Dexfenfluramine at a dose of 30 mg suppressed food intake to the same degree as fenfluramine 60 mg, suggesting that the greater part of the anorectic activity of the racemic mixture lies in the d-isomer (Silverstone T., *Drugs* 43 (6):820-836. 1992). Thus, a dose equivalent to the 30 mg/day dose of dexfenfluramine would be about 60 mg/day of racemic fenfluramine, which is used in the formulations disclosed herein. Thus, in preferred embodiments of the invention, the maximum daily dose is not more than about 26 mg/day fenfluramine as a free base or pharmaceutically acceptable salt (for example, 30 mg/day fenfluramine hydrochloride), with a daily dose of less than about 0.8 mg/kg/day, 0.7 mg/kg/day, 0.6 mg/kg/day, 0.5 mg/kg/day, about 0.4 mg/kg/day, about 0.3 mg/kg/day, about 0.25 mg/kg/day or about 0.2 mg/kg/day to about 0.1 mg/kg/day, about 0.05 mg/kg/day, or about 0.01 mg/kg/day is employed. Put differently, a preferred dose is not more than about 30 mg/day, and less than about 1 to about 0.01 mg/kg/day. Such a dose is less than the daily dose of fenfluramine suggested for administration to achieve weight loss.

The fenfluramine active agent may be administered as a suitable formulation that includes the fenfluramine active agent in a pharmaceutically acceptable vehicle. In some aspects, the method may include administering the fenfluramine active agent at a concentration ranging from 1 mg/mL to 5 mg/mL of fenfluramine present either as a free base or pharmaceutically acceptable salt or conjugate and providing that to the patient over a period of days, weeks or months on a once a day, twice a day, three times a day or four times a day basis wherein the dose is provided to the patient at a level of 0.2 mg/kg/day or 0.7 mg/kg/day up to a maximum of 26 mg per day fenfluramine either as a free base or in a pharmaceutically acceptable salt or conjugate. The dosing is preferably provided at twelve-hour intervals twice a day whereby an aspect of the invention is to reduce convulsive seizure frequency by 50% or more, 60% or more, 70% or more, 80% or more, 90% or more, 95% or more, or completely eliminate seizures in the patient over a period of 10 days, 20 days, 30 days, 50 days, 100 days or more.

According to another aspect of the present invention, the subject may be on, or may be starting on, a ketogenic diet. By "on a ketogenic diet" is meant that the patient consumes nutrition in the form of ketogenic meals, such as ketogenic breakfasts, lunches and dinners. The ketogenic diet, comprised mainly of lipid, has been used for the treatment of epilepsy in children, particularly myoclonic and akinetic seizures (Wilder, R. M. Effect of ketonuria on the course of epilepsy. *Mayo Clin. Bull.*, 1921, 2:307-ff), and has proven effective in cases refractory to usual pharmacological means (Freeman, J. M., E. P. G. Vining. Intractable epilepsy. *Epilepsia*, 1992, 33:1132-1136). Since the early 1990's, when research studies and clinical trials in children demonstrated efficacy of a ketogenic diet in drug-resistant patients and particular pediatric epilepsy syndromes, worldwide interest in the use of ketogenic diets to manage drug-resistant epilepsy in adults has been increasing. Approximately 19.5 million people with epilepsy have seizures uncontrolled by medications. There is also general agreement that patients with infantile spasms (West syndrome), Lennox-Gaustat syndrome, Dravet syndrome, Angelman syndrome (particularly with the LGIT) and myoclonic-astatic epilepsy benefit from a trial of diet therapy once their epilepsy has become refractory to medication (Nangia et al., 2012, Thibert et al., 2012). Williams, et al., op. cit.). Ketogenic diet therapy offers a needed adjunct strategy for management of status epilepticus. It has the potential advantages of working quickly and synergistically with other concurrent treatments, is relatively easy to start, monitor, and maintain in the controlled intensive care unit setting with close follow up, and it does not contribute to hemodynamic instability seen with anesthetic agents used to treat refractory status epilepticus.

Either oral or parenteral administration of free fatty acids or triglycerides can increase blood ketones, provided that carbohydrate and insulin are low to prevent re-esterification in adipose tissue. Rats fed diets comprised of 70% corn oil, 20% casein hydrolysate, 5% cellulose, 5% McCollums salt mixture, develop blood ketones of about 2 MM. Substitution of lard for corn oil raises blood ketones to almost 5 mM (Veech, unpublished). While cellulose is a glucose polymer and thus a carbohydrate, it is not digestible by humans and is not excluded from a ketogenic diet. Non-digestible carbohydrates are often referred to as dietary fiber and are used as bulking agents as well as thickening agents.

An example of a traditional 1500 calorie/day ketogenic diet recommended by the Marriott Corp. Health Care Services, Pediatric Diet Manual, Revised August 1987 as suitable for a 4-6 year old epileptic child contained from 3:1 to 4:1 g of fat for each g of combined carbohydrate and protein. At each of 3 meals of the ketogenic diet the patient must eat 48 to 50 g fat, only 6 g protein and 10 to 6.5 g carbohydrate. In practice this means that at each meal the child must eat the equivalent of 32 g of margarine per day (about ¼ stick) and drink 92 g of heavy cream (about 100 ml), comprised mainly as medium chain length triglycerides. The diet forces the body to metabolize fats instead of carbohydrates for energy, thereby elevating the level of acetoacetate and D-3-hydroxybutyrate in the blood. These compounds are referred to as "ketone bodies," thus the term "ketogenic" is used to describe the diet.

Diet adherence and compliance remain significant barriers to successful ketogenic diet implementation and as well as to adequate controlled assessments of efficacy in the clinic. A meta-analysis of 11 studies of ketogenic diets in adults reported a combined adherence rate of 45% for all types of ketogenic diets, 38% for the classic KD and 56% for the modified Adkins diet (typically composed of a net 10-20 g/day carbohydrate limit—equivalent to a ratio of 1-2:1 of fat to protein and carbohydrates) (Ye et al., *J. Clin. Neurol.* 2015 January; 11(1):26-31). Similarly, a recent observational study of 139 adult patients treated with ketogenic diets, 48% (67 of 139) discontinued the diet (39%) or were lost after initial follow up (9%) with approximately half of patients citing difficulty with compliance or restrictiveness as the reason for stopping. (Williams, et al. op. cit.) The brain accounts for approximately 20 percent of glucose consumption in the body and it tightly regulates the energy supply it requires and the ketogenic diet mimics starvation (i.e., being deprived of a source of glucose as an energy source), causing the body to shift into a metabolic state called ketosis (metabolizing fat as the predominant energy source). One cause of non-compliance or abandonment of the ketogenic diet is carbohydrate craving which results from brain signals that cause craving of the foods containing the nutrient perceived as lacking.

Normally, human bodies are fueled by carbohydrates; ingested carbohydrates are broken down into glucose, which is mainly transported and used as energy or stored as glycogen in liver and muscle tissue. When deprived of dietary carbohydrates (usually below 50 g/day for an adult), the liver becomes the sole provider of glucose to feed bodily organs, especially the brain which, as mentioned above, accounts for ~20% of total energy consumption. However, in some patients the perceived energy imbalance results in cravings, sometimes intense, for carbohydrates. In some patients the cravings subside over time as the body and brain adjust to the new energy balance, however, in other patients the craving for carbohydrates continues. To be successful on a ketogenic diet, a patient must avoid or strictly limit the amount of carbohydrates consumed; the consequence of non-adherence is that the body shifts back to glucose metabolism and the anti-seizure benefits subside, and cravings continue.

The brain maintains a balance between excitation and inhibition which is mediated through two main neurotransmitters, the excitatory glutamate and the inhibitory GABA. Excessive glutamate signaling, which occurs in stroke, seizures and neurodegeneration, results in excitotoxicity. While the exact mechanism of action of the ketogenic diet is not well understood, one long-standing hypothesis is that ketone bodies may act directly as pharmacological agents, although possible targets have not been elucidated. Recently, glutamate transport into synaptic vesicles by the vesicular glutamate transporter, VGLUT2, was found to be inhibited by the ketone body acetoacetate (Juge N, et al. *Neuron.,* 2010, 68:99-211) at concentrations that are expected during the ketogenic diet. In cultured neurons exposed to acetoacetate, glutamate release decreased; thus, inhibition of glutamate signaling by acetoacetate may reduce neuronal excitability. Earlier work suggested that increased production of the inhibitory neurotransmitter GABA might result from changes in brain metabolism produced by ketogenic diet. Without being bound by theory, it is hypothesized that glutamate recycling via glutamine becomes more efficient when ketone bodies are available, and that this may improve GABA resynthesis for inhibitory neurotransmission even more than it affects glutamate repackaging for excitatory neurotransmission. The higher GABA production would be expected to increase inhibitory signaling in the brain, though in rodents, elevations in total brain GABA levels have not been observed. Such changes in GABA signaling may complement the hypothesized alteration in glutamate signaling produced by acetoacetate. (Lutas and Yellen, *Trends Neurosci.,* 2013, January; 36(1):32-40).

In order to be effective for this purpose, however, the patient must strictly observe the diet. Vitamin and mineral supplements are included in the diet to make it nutritionally complete, since the diet is very high in fat, low in proteins, and requires the near elimination of carbohydrates. Each patient's diet is mathematically calculated based on the age, size, and activity level of the patient. Patients normally follow the diet for one to two years, at which time the patient is slowly weaned onto a normal diet. The diet has been found to be particularly effective with epileptic children. Major drawbacks are that the diet is not very palatable and that patient compliance demands complete commitment on the part of the patient and his or her family. Moreover, the diet's high fat content might increase the risk of vascular diseases, such as atherosclerosis in long-term use.

In the present invention, the effective dose of a compound may be administered alone or in combination with a non-pharmacological therapy to a patient with Dravet syndrome. Combination therapeutic methods are methods where a formulation having an effective dose of a compound may be used in combination with an additional therapy. As used herein, a dose of an agent, e.g., fenfluramine, refers to a therapeutically effective dose of the subject formulation containing the agent. The terms "agent," "compound," and "drug" are used interchangeably herein. In one embodiment, a fenfluramine formulation having an effective amount of active agent can be administered alone or in conjunction with a low carbohydrate diet, such as a ketogenic diet. As used herein, an "effective amount" is an amount of a subject compound that, when administered to an individual in one or more doses, in monotherapy or in combination therapy, is effective to reduce the occurrence of seizures by about 20%, at least about 30%, at least about 40%, at least about 50%, at least about 60%, at least about 70%, at least about 80%, or at least about 90%. In some embodiments, the subject method further includes co-administering concomitantly with the ketogenic diet a dose of fenfluramine. In some instances, the method includes administering the compound to a subject, e.g., a patient, on a ketogenic diet. In some embodiments, the method further includes administering a ketogenic diet to a patient.

The terms "co-administration" and "in combination with" include the administration of two or more therapeutic agents or therapies either simultaneously, concurrently or sequentially within no specific time limits. In one embodiment, a therapeutic agent, e.g., an amount of fenfluramine, is present in the subject's body at the same time or exerts a biological or therapeutic effect at the same time as another therapy, e.g., a ketogenic diet. In one embodiment, the therapeutic agent, e.g., an effective dose of fenfluramine, and non-pharmacological therapy, e.g., a ketogenic diet, are administered at the same time. The effective dose of the formulation of fenfluramine may be administered at the same time with a meal of the ketogenic diet. In other embodiments, the therapeutic agent and non-pharmacological therapy are administered at different times. The effective dose of the fenfluramine formulation may be administered, e.g., before or after a meal of the ketogenic diet. In certain embodiments, a first therapeutic agent or a therapy can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent or therapy.

"Concomitant administration" of a therapeutic drug or non-pharmacological therapy means administration of the compound and additional therapy at such time that both the drug and the non-pharmacological therapy of the present invention will have a therapeutic effect. Such concomitant administration may involve concurrent (i.e. at the same time), prior, or subsequent administration of the drug with respect to the administration of a non-pharmacological therapy. Routes of administration of the compound may vary, where representative routes of administration are described below. A person of ordinary skill in the art would have no difficulty determining the appropriate timing, sequence and dosages of administration for particular drugs or therapies of the present disclosure.

In some embodiments, a subject compound, e.g., fenfluramine, and at least one additional compound or therapy, e.g., a meal of a ketogenic diet, are administered to the subject within twenty-four hours of each other, such as within 12 hours of each other, within 6 hours of each other, within 3 hours of each other, or within 1 hour of each other. In certain embodiments, the compound and therapy are administered within 1 hour of each other. In certain embodiments, the compound and therapy are administered substantially simultaneously. By administered substantially simultaneously is meant that the compound and therapy are administered to the subject within about 10 minutes or less of each other, such as 5 minutes or less, or 1 minute or less of each other.

A method of the present invention can be practiced on any suitable subject. A subject of the present invention may be a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

A method of the present invention can be practiced on any appropriately diagnosed patient. In a typical embodiment of the present invention, the patient is an adult, or is aged about 18 or less, about 16 or less, about 14 or less, about 12 or less, about 10 or less, about 8 or less, about 6 or less or about 4 or less to about 0 months or more, about 1 month or more, about 2 months or more, about 4 months or more, about 6 months or more or about 1 year or more. Thus, the diagnosed patient is typically about one month old or older when treated.

The dose of fenfluramine administered in the methods of the present invention can be formulated in any pharmaceutically acceptable dosage form, i.e., formulation, including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

The dosage form of fenfluramine employed in the methods of the present invention may be a liquid dosage form. In some instances, the liquid dosage form is an aqueous liquid dosage form. Liquid dosage forms are available orally as solutions, suspensions, or emulsions. In an aspect of the invention, the fenfluramine formulation is administered as a liquid formulation by use of an oral syringe graduated for precise measurement of the liquid formulation. In some instances, the formulation is substantially free of oil, a non-aqueous solvent, and undissolved particles.

The liquid oral solution dosage form may be suitable for administering a therapeutically effective dose of fenfluramine to a subject based on the condition, sex, and overall disease state of the subject. In some instances, the liquid oral solution dosage form may be suitable for age-based or weight-based dosing. The oral solution dosage form may be suitable for both pediatric and adult populations. In some instances, the oral liquid dosage forms are used by patients who experience difficulty in swallowing.

According to the present invention, there is provided a therapeutically effective dose of a formulation containing a fenfluramine active agent. In some instances, the formulation may include an effective amount of a therapeutic agent suitable for a single administration to provide a therapeutic effect. A therapeutically effective dose may be any variable liquid dose volume that can be measured and administered. In some instances, a range of dose volumes includes volumes suitable for administration to pediatric populations. In certain embodiments, a range of dose volumes includes 0.2 mL to 12 mL, such as, for example, 0.5 mL to 6 mL. In some instances, the dosage volume of the present invention is compatible in carbohydrate caloric content with a ketogenic diet.

The dosage form of fenfluramine employed in the methods of the present invention can be prepared by combining a fenfluramine active agent with one or more pharmaceutically acceptable diluents, carriers, adjuvants, buffering agents, desired excipients and the like in any order of admixing and in a manner known to those skilled in the art of pharmaceutical formulation. Liquid dosage forms can comprise one or more optional pharmaceutical excipients including suspending agents (e.g., gums, xanthans, celluloses and surfactants), solubilizers (e.g., ethanol, water, glycerin, PEG and propylene glycol), surfactants (e.g., sodium lauryl sulfate, Spans, Tweens, and cetyl pyridine), preservatives, (e.g., parabens, sorbates acid, benzoic acid), antioxidants (e.g., ascorbic acid, sodium metabisulfite) anticaking agents, anti-foaming agents (e.g., simethicone), chelating agents (e.g., EDTA), a colorant, a flavor, flavor-aid such as acidifying agent (e.g., citric acid or tartaric acid), or cooling agent (e.g., menthol, xylitol), or a pharmaceutically compatible vehicle or carrier.

An aspect of a formulation according to embodiments of the present invention is a sweetener. The term "sweetener" refers to a sweetener, preferably a natural or artificial sweetener, which his added to formulations according to the present invention in order to render the formulation more palatable. In certain embodiments, the sweetener selected for the fenfluramine formulation, as well as the amount of the sweetener in a formulation, is compatible with a ketogenic diet. According to embodiments of the invention, the carbohydrate caloric content of the sweetener ranges from zero to 40 calories from carbohydrates per 100 g of the formulation. The sweetener may be a high-intensity low calorie or a non-caloric sweetener. Sweeteners according to the present invention may include, for example, aspartame, saccharin, acesulfame potassium, cyclamates, sucralose, among numerous other synthetic sweeteners, natural sweeteners such as *stevia* and thaumatin, sugar alcohols (polyols) such as mannitol, xylitol, maltitol, erythritol and isomalt), as well as sugar based sweeteners such as sucrose/water solutions (USP sucrose syrup, about 85% by weight sucrose and about 15% by weight water), maltose, corn syrup, fructose syrup and related fruit syrup sweeteners, among others. The concentration of sweetener in the formulation may range from 0.1% (1 mg/ml) to 4% (40 mg/ml).

The formulation may further include flavoring agents. Flavoring agents may increase the overall flavor, taste and desirability of the formulation. Suitable flavoring agents include, for example, chocolate, peppermint, spearmint, grape, cherry, strawberry, orange, lemon, root beer, watermelon, etc. or any other flavorings stable at a desired pH or temperature. The dosage forms may include flavoring agents at a concentration ranging from 0.05% (0.5 mg/ml) to 1% (10 mg/ml), such as, for example, 0.05% (0.5 mg/ml) to 0.1% (1 mg/ml).

In some instances, the formulation includes a pH modifying agent, e.g., a buffering agent. A pH modifying agent refers to any pharmaceutically appropriate agent that modulates, alters, or adjusts the pH of a formulation. By buffering agent is meant any pharmaceutically appropriate agent or agents that, when formulated or delivered with the subject formulation, functions to maintain the pH of the formulation. The concentration of buffer may be 0.01 molar to 0.5 molar, such as 0.03M. A suitable pH range may include a pH of 4.5 to 6.5, such as 4.5 to 5.5 and 5.0 to 5.1.

Suitable pH modifying agents may include, but are not limited to, sodium bicarbonate, potassium bicarbonate, magnesium hydroxide, magnesium oxide, magnesium lactate, magnesium gluconate, other magnesium salts, aluminum hydroxide, aluminum hydroxide/sodium bicarbonate coprecipitate, a mixture of an amino acid and a buffer, a mixture of aluminum glycinate and a buffer, a mixture of an acid salt of an amino acid and a buffer, and a mixture of an alkali salt of an amino acid and a buffer. Additional pH modifying agents include, but are not limited to, magnesium carbonate, magnesium silicate, calcium acetate, calcium glycerophosphate, calcium chloride, calcium hydroxide, calcium lactate, calcium carbonate, calcium bicarbonate, and other calcium salts. Buffering agents of interest may include sodium citrate (in combination with citric acid), sodium tartarate (in combination with tartaric acid), sodium acetate (in combination with acetic acid), sodium carbonate (in combination with sodium bicarbonate), sodium polyphosphate, potassium polyphosphate, sodium pyrophosphate, potassium pyrophosphate, disodium hydrogenphosphate, dipotassium hydrogenphosphate, trisodium phosphate, tripotassium phosphate, potassium metaphosphate. In certain embodiments, the buffering agent is a citrate buffering agent or citrate-phosphate buffering agent, depending on, e.g., the target pH. In some instances, the buffering agent is tripotassium citrate and citric acid. Exemplary buffers include citric acid/phosphate buffer, acetate buffer, citrate buffer or phosphate buffer.

Additionally, various additives can be incorporated into such liquid dosage forms to enhance stability, sterility and/or isotonicity (e.g. sugars, sodium chloride, etc). Antimicrobial preservatives, such as ambicin, antioxidants, chelating agents, and additional buffering agents can be added. The formulations may be buffered to a pH within the range of optimal activity of the preservatives. Various antibacterial and antifungal agents such as, for example, parabens (parahydroxybenzoates or 4-hydroxybenzoates), chlorobutanol, phenol, sorbic acid, and the like can enhance prevention of the action of microorganisms. The preservative may be a free acid or a sodium or potassium salt.

Suitable preservatives may include, for example, a paraben (methylparaben, ethylparaben, propylparaben, butylparaben), benzalkonium chloride, benzethonium chloride, benzoic acid, benzyl alcohol, bronopol, cetrimide, chlorhexidine, chlorobutanol, chlorocresol, cresol, imidurea, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, propyl paraben, myristyl gamapicolinium chloride, paraben methyl, paraben propyl and quaternary ammonium compounds.

The present formulation may contain an amount of preservatives effective for preventing microbial growth. A preservative or a combination of preservatives, e.g., the combination of methylparaben and ethylparaben either as free acids or water soluble salts (sodium or potassium salts), may be present in the formulation at concentrations ranging from 0.01% (0.2 mg/ml) to 0.5% (5 mg/ml), such as from 0.01% (0.1 mg/mi) to 0.2% (2 mg/ml) on a free acid basis. In some instances, the formulation includes 0.2% (2 mg/ml) methylparaben in combination with 0.02% (0.2 mg/ml) ethylparaben; or 0.1% (1 mg/ml) methylparaben in combination with 0.01% (0.1 mg/ml) ethylparaben Methylparaben and ethylparaben (either as free acids or water soluble salts) may be present a ratio that ranges from 20:1 to 2:1, e.g., 10:1, (methylparaben:ethylparaben).

Additionally, thickening agents or viscosity modifiers can be used in the formulation. Thickening agents may be used to, for example, reduce settling of particles in suspension, reduce the potential for spillage, improve control during pouring, improve the manufacturing of the formulation, improve palatability of the formulation, and improve delivery of the formulation, for example, by an oral syringe. In some instances, the thickening agent provides a suitable viscosity to the formulation, for example, a viscosity range of 100-200 cP and for example, a viscosity of 150 cP.

Thickening agents for use in the present formulation include polymeric and non-polymeric water-miscible or water-soluble thickening agents. In some instances, the thickening agents for use individually or in combination include methylcellulose, polyethylene glycol (PEG) 400, glycerin, xanthan gum, pregelatinized starch, hydroxyethylcellulose (250 HX), povidone, povidone K-90, and the like. In some instances, the thickening agent may include acetylated distarch adipate, acetylated distarch phosphate, acetylated oxidized starch, acetylated starch, acid treated starch, agar, alginic acid or its pharmaceutically acceptable salts and derivatives, alkaline treated starch, ammonium alginate, arabinogalactan, bleached starch, calcium alginate, carrageenan, dextrin, modified starch, distarch phosphate, enzyme treated starch, gellan gum, guar gum, gum Arabic (acacia), glycerol, hydroxypropyl cellulose, hydroxypropyl distarch phosphate, hydroxypropyl methylcellulose, hydroxypropyl starch, karaya gum, konjac gum, locust bean gum, methyl ethyl cellulose, methylcellulose, polyethylene oxide, monostarch phosphate, oxidized starch, pectin, phosphated distarch phosphate, processed eucheuma seaweed, propane-1,2-diol alginate, copovidone, odium alginate, starch sodium octenylsuccinate, tara gum, tragacanth, or a combination thereof. It should be noted that polysaccharide polymers such as cellulose, or derivatized cellulose are also considered to be carbohydrates, however, given the beta-acetal linkages between the glucose units that compose celluloses, they are not digestible by humans and constitute what is referred to as dietary fiber. Gums such as gum arabic or xanthan gum, are soluble dietary fibers, with complex polysaccharide structures, that are primarily indigestible to both humans and animals. Given their undigestible nature, they are not incompatible with a ketogenic diet as they do not present an appreciable amount of carbohydrate for metabolism. In some embodiments, the formulation comprises a thickening agent which is substantially devoid of digestible carbohydrate.

Thickening agents may be of any grade providing a desired viscosity range, e.g., of 1500-5000 mPa·s (cP) for 1% solution. In certain embodiments, the concentration of the thickening agent ranges from 0.2% (2 mg/ml) to 5% (50 mg/ml), such as from 0.3% (3 mg/ml) to 2% (20 mg/mL), including 0.4% (4 mg/mL) to 1% (10 mg/mL).

The formulation and dosage of the present invention is one that is compatible with a ketogenic diet. In some cases, the total carbohydrate caloric content of a single dose of the formulation ranges from zero to 5 carbohydrate calories. In certain embodiments, a single component of the subject formulation has a carbohydrate caloric content of zero to 2 carbohydrate calories. In some embodiments, the formulation lacks a nutritive/digestible/glycemic carbohydrate.

In some embodiments, the formulation is a liquid fenfluramine formulation, comprising a therapeutically effective amount of a fenfluramine active agent; and a pharmaceutically acceptable vehicle, wherein the formulation does not contain a digestible carbohydrate and reduces carbohydrate craving thus promoting compliance with a ketogenic diet. In some embodiments, the active agent is fenfluramine base or a pharmaceutically acceptable salt or conjugate thereof. In some embodiments, the fenfluramine active agent is a fenfluramine pharmaceutically acceptable salt. In some embodiments, the fenfluramine pharmaceutically acceptable salt is fenfluramine hydrochloride.

In some embodiments, the liquid fenfluramine formulation is an aqueous formulation. In some embodiments, the aqueous formulation comprises a sweetener. In some embodiments, the sweetener is at least a low-calorie sweetener. In some embodiments, the sweetener is a not a source of digestible carbohydrate. In some embodiments, the sweetener is a non-caloric sweetener. In some embodiments, the sweetener is sucralose.

In the present invention, fenfluramine may be stable in an aqueous solution, as described above. In some instances, the fenfluramine formulation is stable for 6 to 60 months when stored at room temperature or at temperatures ranging from 5° C. to 60° C. In some instances, the formulation is formulated in a pH ranging from 4 to 7. The formulation may be stored in any container suitable to maintain the stability of the formulation during its shelf life.

The dose of fenfluramine to be used in a method of the present invention can be provided in the form of a kit, including instructions for using the dose in one or more of the methods of the present invention. In certain embodiments, the kit can additionally comprise a dosage form comprising one or more co-therapeutic agents.

The invention is further illustrated in the following Examples.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Components of the Drug Product [Fenfluramine, Oral Solution]

Drug Substance

Compatibility of the Drug Substance with the Excipients

The compatibility of fenfluramine hydrochloride in solution with the formulation excipients has been established through development stability studies. Multiple formulations including various combinations of the ingredients were evaluated at long-term and accelerated storage conditions. In addition, results to date from ICH-compliant stability studies of the intended commercial formulation provide further evidence of the compatibility of the drug substance with the formulation excipients.

Physicochemical Characteristics of the Drug Substance

The physicochemical properties of fenfluramine hydrochloride drug substance are summarized below. Properties that are relevant to the performance and manufacturability of the drug product are discussed below.

Solid State

Fenfluramine hydrochloride is a crystalline material that exists as a single form (Form 1) with a needle-like morphology. The drug substance is chemically and physically stable in the solid state and no other polymorphs have been observed in a polymorph screening study or in the accelerated and long-term stability studies.

Aqueous Solubility

The drug substance aqueous solubility varies moderately as a function of pH. At 25° C., the solubility ranges from approximately 25 mg/ml at pH 1.7 to over 50 mg/mL at pH 6.7. With solubility of more than 10-fold higher than its concentration in the drug product, precipitation of the drug substance out of solution is unlikely to occur under normal storage conditions, including long-term refrigeration. Drug product formulation stored at 5° C. for more than one month and for several days at −20° C. did not show any significant change in fenfluramine assay.

The solubility at physiological temperature (37° C.) and in the pH range of 1.7 to 6.7 varies between 54 mg/mL and 96 mg/mL.

Particle Size

Fenfluramine hydrochloride drug substance is non-micronized. The range of particle size parameters obtained from five GMP batches (two clinical batches manufactured by Onyx, and three registration batches manufactured by Aptuit) is listed in Table 1. Due to the high solubility of fenfluramine hydrochloride relative to its concentration in the formulation, particle size is not expected to have a significant effect on the drug product manufacturing process. This was confirmed by manufacturing experience that consistently demonstrated rapid dissolution of the drug substance in the formulation vehicle. In addition, an experimental batch of drug substance with a median particle size (D50) of 60 μm and ninetieth percentile (D90) of 250 μm was evaluated in comparison to micronized portions of the same batch and no difference was observed in the time needed for complete dissolution in the formulation vehicle.

TABLE 1

Particle size range of fenfluramine hydrochloride clinical and registration batches

| Batch | D10 (μm) | D50 (μm) | D90 (μm) |
|---|---|---|---|
| 1 | 1.19 | 6.79 | 26.25 |
| 2 | 1.28 | 8.92 | 32.08 |
| 3 | 2.53 | 8.20 | 27.04 |
| 4 | 2.01 | 6.16 | 18.96 |
| 5 | 2.24 | 6.99 | 23.01 |

Solution Stability

Forced degradation studies indicated the API was very stable in aqueous solution. Thermal stability of buffered aqueous solutions of fenfluramine hydrochloride ranging from 0.5 mg/mL to 5 mg/mL concentration was investigated during early development. The data, provided in Table 2, Table 3 and Table 4, show that fenfluramine hydrochloride solution is stable for at least 6 months when stored at 60° C. at pH 6.8.

TABLE 2

Stability of Fenfluramine Hydrochloride 0.5 mg/mL
Buffered Aqueous Solution, pH 6.8
Initial:
Appearance: A clear solution. Free from visible contamination.
Assay: 99.2% of theoretical
Purity: 99.9%

| Stability Results | 40° C. | 60° C. |
|---|---|---|
| T = 4 Weeks | Appearance: clear solution, free from visible contamination<br>Assay: 102.5% of initial<br>Purity: 99.8% | Appearance: clear solution, free from visible contamination<br>Assay: 102.1% of initial<br>Purity: 99.8% |
| 8 Weeks | Appearance: clear solution, free from visible contamination<br>Assay: 101.9% of initial<br>Purity: 99.8% | Appearance: clear solution, free from visible contamination<br>Assay: 101.9% of initial<br>Purity: 100.0% |
| 12 Weeks | Appearance: clear solution, free from visible contamination<br>Assay: 101.9% of initial<br>Purity: 99.7% | Appearance: clear solution, free from visible contamination<br>Assay: 100.0% of initial<br>Purity: 99.7% |
| 16 Weeks | Appearance: clear solution, free from visible contamination<br>Assay: 100.0% of initial<br>Purity: 99.9% | Appearance: clear solution, free from visible contamination<br>Assay: 100.0% of initial<br>Purity: 99.9% |
| 6 Months | Appearance: clear solution, free from visible contamination<br>Assay: 100.0% of initial<br>Purity: 99.8% | Appearance: clear solution, free from visible contamination<br>Assay: 100.9% of initial<br>Purity: 99.8% |

TABLE 3

Stability of Fenfluramine Hydrochloride 2.5 mg/mL
Buffered Aqueous Solution, pH 6.8
Initial:
Appearance: clear solution, free from visible contamination
Assay: 99.1% of theoretical
Purity: 99.9%

| Stability Results | 40° C. | 60° C. |
|---|---|---|
| 4 Weeks | Appearance: clear solution, free from visible contamination<br>Assay: 101.6% of initial<br>Purity: 99.8% | Appearance: clear solution, free from visible contamination<br>Assay: 100.8% of initial<br>Purity: 99.8% |
| 8 Weeks | Appearance: clear solution, free from visible contamination<br>Assay: 100.4% of initial<br>Purity: 99.8% | Appearance: clear solution, free from visible contamination<br>Assay: 100.8% of initial<br>Purity: 99.8% |
| 12 Weeks | Appearance: clear solution, free from visible visible contamination<br>Assay: Not reported<br>Purity: Not reported | Appearance: clear solution, free from visible contamination<br>Assay: 108.1% of initial<br>Purity: 99.7% |
| 16 Weeks | Appearance: clear solution, free from visible contamination<br>Assay: 98.8% of initial<br>Purity: 99.9% | Appearance: clear solution, free from visible contamination<br>Assay: 101.6% of initial<br>Purity: 99.9% |

TABLE 3-continued

Stability of Fenfluramine Hydrochloride 2.5 mg/mL
Buffered Aqueous Solution, pH 6.8
Initial:
Appearance: clear solution, free from visible contamination
Assay: 99.1% of theoretical
Purity: 99.9%

| Stability Results | 40° C. | 60° C. |
|---|---|---|
| 6 Months | Appearance: clear solution, free from visible contamination<br>Assay: 102.8% of initial<br>Purity: 99.8% | Appearance: clear solution, free from visible contamination<br>Assay: 107.6% of initial<br>Purity: 99.7% |

TABLE 4

Stability of Fenfluramine Hydrochloride 5 mg/mL
Buffered Aqueous Solution, pH 6.8
Initial:
Appearance: clear solution, free from visible contamination
Assay: 99.6% of theoretical
Purity: 99.9%

| Stability Results | 40° C. | 60° C. |
|---|---|---|
| 4 Weeks | Appearance: clear solution, free from visible contamination<br>Assay: 101.4% of initial<br>Purity: 99.8% | Appearance: clear solution, free from visible contamination<br>Assay: 101.6% of initial<br>Purity: 99.8% |
| 8 Weeks | Appearance: clear solution, free from visible contamination<br>Assay: 100.4% of initial<br>Purity: 99.8% | Appearance: clear solution, free from visible contamination<br>Assay: 98.8% of initial<br>Purity: 99.8% |
| 12 Weeks | Appearance: clear solution, free from visible contamination<br>Assay: 106.4% of initial<br>Purity: 99.8% | Appearance: clear solution, free from visible contamination<br>Assay: 98.2% of initial<br>Purity: 99.8% |
| 16 Weeks | Appearance: clear solution, free from visible contamination<br>Assay: 99.8% of initial<br>Purity: 99.9% | Appearance: clear solution, free from visible contamination<br>Assay: 97.2% of initial<br>Purity: 99.9% |
| 6 Months | Appearance: clear solution, free from visible contamination<br>Assay: 102.6% of initial<br>Purity: 99.7% | Appearance: clear solution, free from visible contamination<br>Assay: 107.6% of initial<br>Purity: 99.7% |

Excipients

The excipients in fenfluramine oral solution formulation include preservatives, viscosity building agent, sweetener, buffering agents and a flavoring agent. All excipients used in the formulation are commonly used excipients in approved pharmaceutical products. Compatibility with the drug substance in solution has been demonstrated through real-time stability data.

The properties of each excipients that may affect the performance and manufacturability of the drug product formulation are briefly discussed below.

Methylparaben Sodium

Methylparaben sodium (sodium methyl p-hydroxybenzoate) is a compendial excipient with USP-NF and Ph. Eur. monographs. It is the sodium salt of methyl 4-hydroxybenzoic acid. Methylparaben is a preservative commonly used in oral, topical and injectable pharmaceutical formulations, both as free acid and sodium salt and exhibits its antimicrobial activity in the pH range of 4-8. Paraben preservatives are typically used in combination due to the known synergy in their antimicrobial effects.

Methylparaben sodium is used in the formulation at a concentration of 0.23% (equivalent to 0.2% methylparaben), in combination with 0.023% ethylparaben sodium (equivalent to 0.02% ethylparaben). These preservative levels were selected based on data from preservative efficacy testing (PET). Methylparaben concentration in fenfluramine drug product and placebo is within the range used in FDA-approved oral pharmaceutical products listed on the inactive ingredient database.

The solubility of methylparaben and its salts is pH dependent, with lower solubility in acids and higher solubility in alkaline media. Solubility of the free acid in water is 0.25% (1 in 400) at 20° C. and 0.30% at 25° C. (Pub Chem). Methylparaben sodium has a higher aqueous solubility than the free acid and was found to dissolve more rapidly in the drug product formulation.

The sodium salt of methylparaben was selected to minimize the risk of preservative precipitation if the product is inadvertently stored at cold temperatures for an extended period of time. With the sodium salts of methyl- and ethylparaben (in combination), no sign of precipitation was observed in the drug product formulation after one month of storage at 5° C. during early development. However, some precipitation (up to 20% of methylparaben) was later observed in temperature cycling studies with no effect of preservative efficacy. No precipitation has been observed in the long-term storage stability studies.

Methylparaben sodium undergoes hydrolysis at high pH, but has acceptable stability below pH 6. The preservative degradation was observed to increase at higher pH, consistent with literature data (Kamada, 1973). The pH of the drug product formulation was optimized to minimize the preservative degradation. The intended commercial formulation of fenfluramine oral solution is buffered to a target pH of 5.0 and no significant increase the degradant level has been observed to date, with up to 24 months stability data in the representative clinical formulation and 18 months data in the intended commercial formulation.

Methylparaben sodium is moderately hygroscopic and may contain up to 5% water. The manufacturing process requires correction for the water content.

Methylparaben sodium has a slightly burning taste.

Ethylparaben Sodium

Ethylparaben sodium (sodium ethyl p-hydroxybenzoate) is a compendial excipient with USP-NF and Ph. Eur. monographs. It is the sodium salt of ethyl 4-hydroxybenzoic acid. Ethylparaben and its sodium and potassium salts are used as preservatives in oral and topical pharmaceutical formulations. Ethylparaben was selected for use as the second paraben preservative in fenfluramine oral solution due to its higher aqueous solubility compared to the more commonly used propylparaben, since the parabens' aqueous solubility decreases with the chain length.

Until recently ethylparaben was available in the US only as a free acid. In Europe, both the free acid and sodium salt have been available and are commonly used in pharmaceutical products. The solubility of ethylparaben free acid is 0.08% at 25° C. and 0.07% at 20° C. (PubChem). Ethylparaben sodium has a higher aqueous solubility than the free acid and was found to dissolve more rapidly in the drug product formulation. Ethylparaben sodium is used in the formulation at a concentration of 0.023%, in combination with 0.23% methylparaben sodium. These concentrations were selected based on data from preservative efficacy testing (PET). A lower concentration level was also evaluated in the study.

The sodium salts of the parabens were selected to minimize the risk of preservative precipitation if the product is inadvertently stored at cold temperatures for an extended period of time. With the sodium salts of methyl- and ethylparaben (in combination), no sign of precipitation was observed in the drug product formulation after one month of storage at 5° C. during early development. However, some precipitation (up to 5% of ethylparaben) was later observed in temperature cycling studies with no effect of preservative efficacy. No precipitation has been observed in the long-term storage stability studies.

Like methylparaben, ethylparaben degrades in solution by hydrolysis. The rate increases at higher pH. The pH of the drug product formulation was optimized to minimize the preservative degradation while maintaining adequate solubility, and no significant increase in the preservatives degradation product has been observed in long-term stability studies.

The performance of the preservative system in the drug product formulation was confirmed using compendial preservative efficacy testing (Ph. Eur. 5.1.3/USP <51>) for oral products.

Hydroxyethylcellulose (HEC)

Hydroxyethylcellulose is a compendial excipient with a USP, Ph. Eur. and JP harmonized monograph. It is commonly used in pharmaceutical liquid formulations as a viscosity building (thickening) agent and suspending agent, and in solid dosage forms as a binder and coating agent. It is used in fenfluramine oral solution as a thickening agent.

HEC is a nonionic semi-synthetic water-soluble polymer. It is a partially substituted poly(hydroxyethyl) ether of cellulose and is available in different grades, with a wide range of viscosity depending on the degree of substitution and molecular weight. The grade used in fenfluramine oral solution (250HX) has a specified viscosity range of 1500-2500 mPa·s for 1% aqueous solution. Using this high viscosity grade allowed for achieving the target viscosity range for the drug product at 0.5% concentration (5 mg of HEC per ml). The amount is within the range of use in FDA-approved products for oral administration.

HEC dissolves in cold and hot water, but as with other hydrophilic polymers, the particles tend to agglomerate when wetted before completely swelling and then eventually dissolving. It tolerates relatively high concentrations of ionic components and has no known incompatibility with any of the other excipients used in the formulation.

HEC solutions are clear, colorless and tasteless.

HEC is stable in solution but is susceptible to acid hydrolysis at low pH, which may result in a drop in viscosity. Oxidative degradation may occur under alkaline conditions.

Sucralose

Sucralose is a semi-synthetic sweetener approved by the FDA as a non-nutritive sweetener and is commonly used in food products and pharmaceutical formulations. Sucralose is used as a sweetener in fenfluramine drug product at a concentration of 0.1% (1.0 mg/mL), which is within the range used in FDA-approved pharmaceutical products.

Sucralose is water-soluble and its solution is colorless and has a sweet taste.

Flavoring Agent

The cherry flavoring powder SN932130 (International Flavors and Fragrances (IFF), Netherland) is a proprietary mixture of flavoring agents for use in food, beverage and pharmaceutical products. It is used in the formulation at 0.1% (1 mg/mi).

Potassium Citrate

Potassium citrate (tripotassium citrate) is the tripotassium salt of citric acid. It is a compendial excipient with USP-NF and Ph. Eur. monographs. It is used in food, beverages and pharmaceutical products as an alkalizing agent or a buffering agent. Potassium citrate is highly soluble in water and its aqueous solutions are colorless and have saline taste. Potassium citrate is a generally regarded as safe (GRAS) material.

Citric Acid

Citric acid is a GRAS material and a compendial excipient with USP-NF and Ph. Eur. monographs. It is used in food, beverages and pharmaceutical products as a buffering agent, acidifying agent and a flavor aid. It is used in fenfluramine oral solution as a buffering agent in combination with potassium citrate.

Citric acid is readily soluble in water and has a sour taste of which the intensity depends on the concentration.

Water for Irrigation

Water for irrigation, Ph. Eur. (also meets the requirements for sterile water for irrigation, USP) is used as the formulation vehicle and accounts for more than 95% of the drug product composition.

Example 2

Formulation Development [Fenfluramine, Oral Solution]

Overview

Earlier open label clinical studies in Dravet syndrome (DS) were conducted using a solid oral dosage form (capsules containing a blend of API and lactose) for dispersion in a liquid vehicle prior to administration. The subsequent development activities aimed at producing a liquid formulation for oral administration, with a single concentration of fenfluramine hydrochloride that is suitable for pediatric or adult use across the entire dosing range, and is stored in a multi-use bottle at room temperature. Other target product properties and their justification are briefly discussed below.

Aqueous Solution:

An aqueous oral solution is generally considered an acceptable dosage form for children as young as newborns. The liquid dosage form provides flexibility for age-based or weight-based dosing. The target range of dose volumes (0.5 mL to 6 mL) is small enough for administering to young children without compromising accuracy of dose measurement.

Compared to other pediatric oral dosage forms (suspensions, dispersible powders or granules and orally disintegrating tablets), oral solutions have the lowest risk of choking and aspiration due to the absence of solid particles. An oral solution is also most likely to be compatible with gastric and naso-gastric tube administration.

The aqueous vehicle provides acceptable mouth feel.

Preserved:

Aqueous formulations in multi-dose containers require preservation against microbial growth.

Buffered:

A buffering system is required to maintain the pH at an adequate range for preservatives efficacy, solubility and stability.

Sweetened and Flavored:

The drug product is sweetened and flavored to improve acceptability for pediatric patients by masking potential objectionable taste from the active and/or other formulation components, such as preservatives, and the saline taste from the buffering salt.

Slightly Viscous:

Increased viscosity of the liquid formulation reduces the potential for accidental spillage and improves control during pouring to prevent overflow. It is also believed to contribute to taste masking by reducing the contact area with the tongue.

Not Colored:

A red dye was included in the clinical product to ensure blinding of placebo and active solutions. However, for the intended commercial formulation, a coloring agent is unnecessary.

Fenfluramine hydrochloride concentrations between 0.5 and 5 mg/mL were initially evaluated. For accuracy of dose measurement and ease of administration, 2.5 mg/ml was selected as the target concentration for the intended commercial product since it results in dosing volumes of not less than 0.5 ml per dose and not more than 6 ml per dose. Two additional concentrations (1.25 mg/ml and 5 mg/ml) were later developed using the same liquid formulation to enable dose blinding in Phase 3 clinical studies.

The high aqueous solubility of fenfluramine hydrochloride made it possible to formulate an aqueous solution at the target product concentrations.

Forced degradation studies indicated the API was very stable in aqueous solution. This was confirmed by conducting a short-term solution stability study at high temperatures and neutral pH (pH 6.8 buffered solution). Solution stability data from the thermal stress study covered a range of concentrations from 0.5 mg/ml to 5 mg/ml. Fenfluramine was stable for at least 6 months when stored at 60° C. in pH 6.8 aqueous solution.

Given the API aqueous stability, the formulation development therefore focused on selecting functional excipients to impart the target product properties discussed earlier in this section, and on identifying suitable concentration ranges for these excipients.

In selecting the excipients, choices were intentionally limited to excipients that fit the constraints of a ketogenic diet, which some patients are put on to help control seizures. Short term stability studies of early prototype formulations were conducted to evaluate compatibility of the API with potential formulation excipients in aqueous solution. The stability was later confirmed in longer term stability studies in parallel with the clinical program. The available data provide confidence that the proposed formulation is stable on long term storage.

Selection of the Formulation Vehicle

A buffered aqueous vehicle was selected due to the good solubility of drug substance in water and solution stability.

Development of the Preservative System

Aqueous solutions in multi-dose containers generally require antimicrobial preservation. Two preservative systems (sorbic acid and a paraben combination) that are commonly used in aqueous oral liquids were evaluated for preservative efficacy and stability in fenfluramine oral solution prototypes. The formulations containing the preservative systems were compared also to a preservative-free formulation. The formulations were buffered to a pH within the range of optimal activity of the preservatives. All five prototype formulations initially passed the criteria for preservation of an oral liquid as outlined in Ph. Eur 5.1.3; i.e. at least a three (3) log reduction for bacterial inoculations and a one (1) log reduction for fungi at 14 days, with no increase at 28 days. Table 5 summarizes performance of each individual development batch's performance Sorbic acid containing formulations performed no better than the preservative free formulation, suggesting that this preservative provided no functional preservation efficacy in the formulation. The formulations containing parabens were better preserved against fungi, yeast and mold than the preservative free formulation and was more likely to provide better preservation for the more demanding in-use and end of shelf life testing. Therefore, a parabens-based preservative system was selected for further development and optimization.

TABLE 5

Preservative Efficacy of Fenfluramine Hydrochloride Oral Liquid Prototype Formulations

| Description (Batch Number) | Result |
| --- | --- |
| High Level Parabens (DB501625.01) | 5 and 6 log reduction of all bacterial and fungal inoculations at both 14 and 28 days. |
| Low Level Parabens (DB501625.02) | 5 log reduction of all bacteria at 14 days. Slight weakness against fungi at 14 days, improving at 28 days |
| High level Sorbate (DB501625.03) | 5 log reduction of all bacteria at 14 days. Weak against fungi |
| Low level Sorbate (DB501625.04) | As per High level Sorbate, even weaker against C. Albicans and A. brasilensis |
| preservative free (DB501625.05) | Comparable to Low level Sorbate but with a better reduction in C. Albicans |

The parabens (parahydroxybenzoates or 4-hydroxybenzoates) are broad spectrum preservatives that are effective over a pH range of 4-8. Combinations are typically used due to synergistic effects. The combination of methylparaben and ethylparaben were evaluated in the prototype formulations of fenfluramine hydrochloride solution. Methylparaben is the most commonly used and most water soluble of the paraben preservatives. Ethylparaben, a less commonly used paraben, was included because of its higher aqueous solubility when compared to longer chain alternatives (propylparaben and butylparaben). Two levels of preservative concentrations were evaluated: 0.2% (2 mg/ml) methylparaben in combination with 0.02% (0.2 mg/ml) ethylparaben; and 0.1% (1 mg/ml) methylparaben in combination with 0.01% (0.1 mg/ml) ethylparaben. Although prototypes at both levels met the acceptance criteria for Ph. Eur. 5.1.3 at time zero, a weakness was consistently observed in the low level prototypes with respect to fungal species, which suggests that these prototypes may not be able to retain adequate preservation efficacy by the end of their projected shelf-life. Based on these data, the higher preservative level (0.2% methylparaben and 0.02% ethylparaben, on a free acid basis) was selected for the clinical formulation. Long-term stability data for preservative efficacy confirmed the efficacy of the selected preservative level.

Methylparaben and ethylparaben are soluble at the concentrations used in the drug product formulation with a solubility of 2.5 mg/ml and 0.8 mg/ml, respectively. However, difficulties in dissolving the preservatives were observed when the paraben free acids were used. Precipitation was also detected, particularly when prototypes were stored at 2-8° C. Methylparaben and ethylparaben free acids were later replaced with the corresponding sodium salts due to higher solubility and faster dissolution in the formulation vehicle at room temperature, and no dissolution or precipitation issues were observed with the salts during development studies or during long-term stability testing. However, small amounts of precipitate (less than 20% of the methylparaben content and less than 5% of the ethylparaben content) were later observed in temperature cycling studies that involved refrigeration and/or freezing of the drug product. The presence of the precipitate did not impact preservative efficacy and all samples conformed to the PET acceptance criteria. The drug product storage condition is controlled room temperature.

Selection of a Thickening Agent

A viscosity range of approximately 100-200 mPa·s (100-200 cP) at 100 rpm (using a rotating-spindle viscometer) was set as a target for the product because it allows accurate delivery using an oral syringe (no dripping), does not result in potential manufacturing issues, such as excessive air entrapment and potentially improves palatability of the formulation. This range was selected after evaluating commercially available over-the-counter pediatric oral liquid products that appeared to have a suitable viscosity. The measured viscosity of the product was approximately 150 mPa·s (150 cP).

Both polymeric and non-polymeric water-miscible or water-soluble thickening agents were initially evaluated. These included a combination of polyethylene glycol (PEG) 400 and glycerin, xanthan gum, pregelatinized starch, hydroxyethylcellulose and povidone. Later, the assessment focused on the hydrophilic polymers xanthan gum, povidone K-90 and hydroxyethyl cellulose due to their wider range of concentration-dependent viscosity compared to liquid excipients such as PEG and glycerin.

To compare the viscosity building effects of the three polymers in the fenfluramine hydrochloride formulation, small batches containing various concentrations of each thickening agent were prepared in buffered and preserved vehicle, to ensure any potential interactions between the thickening agents and other components of the formulation would be accounted for. These experiments were conducted at 1 L scale. The preserved buffered vehicles were stirred to create a vortex and the thickening agents in the form of dry powder were slowly added into the vortex. Visual observation of each polymer's ease of dispersion, tendency to agglomerate and time to reach its maximum viscosity (as a measure of complete dissolution in the vehicle) was recorded, and viscosity of the solutions were measured.

All three excipients examined were able to thicken the preserved buffered vehicle to the required viscosity range. Hydroxyethylcellulose took the shortest time to hydrate and reach final viscosity, dispersing evenly into the solution when sprinkled into a vortex and taking approximately 10 minutes to hydrate. Xanthan gum took a similar time to add to the bulk solution, but took nearly 45 minutes to reach final viscosity. The xanthan gum proved difficult to hydrate evenly without using high shear mixing, with some un-hydrated lumps occasionally leading to batches being discarded. Povidone took significantly longer to add to solution due to the larger amount of powder required and formed clumps that took several hours' mixing to disperse. Once dispersed, Povidone took approximately 10 minutes to reach a final viscosity.

Prototypes with the three different thickeners at the levels required for the target viscosity (0.3%, 5% and 0.5% for xanthan gum, povidone K-90 and hydroxyethylcellulose 250 HX respectively were assessed for interference in the HPLC assay method being developed for the drug product. The povidone containing formulation resulted in blockage and damage to the HPLC column, likely due to the relatively high concentration of polymer. Further dilution of the product would have resulted in lower sensitivity of the method.

Based on the viscosity data, lack of interference with the fenfluramine analytical method and processing observations, hydroxyethylcellulose was selected as the thickener for drug product formulation because it was the easiest to disperse and hydrate, the quickest to dissolve and the most efficient in terms of viscosity increase per amount added. The concentration selected is 0.5%, which provide a viscosity of approximately 150 cP.

Selection of Sweetener

Since a ketogenic (low carbohydrate) diet may be used in epilepsy patients whose seizures are refractory to conventional antiepileptic drug therapy, the sweetener selection effort for fenfluramine hydrochloride oral solution focused on high-intensity non-caloric, or low-calorie sweeteners, including mannitol, maltitol, maltodextrin, sorbitol and sucralose. Sugar alcohols (polyols) were quickly eliminated due to their potential laxative effects and limited availability of data on their acceptability in children. Sucralose was selected because of its broad acceptability, high sweetness power allowing its use at very low concentrations, and good taste profile (no aftertaste). Sucralose concentrations in oral liquid product listed on the FDA's inactive ingredients database range from 0.1% to 4%. The concentration selected for fenfluramine hydrochloride (0.1%) is on the low end of the used range and was intended to balance the need for sweetening to make the product palatable to small children against the potential of making it too attractive to the point that risks overdosing.

Selection of Flavoring Agent

Fenfluramine compatibility was evaluated in binary mixtures with strawberry, cherry and orange flavors. Initial development prototypes were formulated with an orange flavor as it is believed that citrus flavors generally have good taste masking properties, especially at acidic pH values. However, at the selected pH range for the formulation, orange flavor did not fully dissolve and caused a slightly hazy appearance. The flavoring agent was changed to cherry, which proved to be compatible with the formulation and resulted in an improved clear appearance. Cherry flavor is a broadly acceptable flavor with a taste profile that is compatible with a broad pH range. A concentration range of 0.05% to 0.5% was evaluated based on the supplier's recommendation and a 0.05% was initially selected for the clinical product because of the general preference for neutral or mild flavors, especially for chronic use. This formulation was packaged in glass bottles and initially assigned a short shelf-life. The concentration was later increased to 0.1%.

Selection of a Buffer System

A pH range of 4.5 to 6.5 was investigated during formulation development studies. Various prototypes were prepared with either citrate buffer or citrate-phosphate buffer, depending on target pH. The prototypes were tested for fenfluramine assay and related substances as well as preservatives assay and related substances on stability, and were visually assessed for precipitation after up to one month refrigeration. Fenfluramine hydrochloride was stable over the entire range of pH, but a degradation product of the paraben preservatives was observed with an increasingly higher magnitude as the formulation pH was increased. Based on initial stability data, a target pH of 5.0 (range: 4.5-5.5) was selected because it minimized the preservatives degradation at long-term and accelerated stability conditions without causing precipitation in product stored at 2-8° C. The buffer components in the drug product formulation are tripotassium citrate and citric acid. Potassium citrate was used instead of sodium citrate to avoid common ion effect with the paraben sodium salts, which may have contributed to precipitation in prototypes containing sodium citrate.

Development Stability Studies

A development stability study was conducted with the selected composition at both ends of the pH range, and with both low and high preservative levels to confirm stability of the clinical formulation. The matrix of compositions evaluated in the formulation development study is presented in Table 6.

TABLE 6

Composition of Preservative Combinations

| | pH of Buffer | Parabens Level |
|---|---|---|
| DB501625.024 | High (pH 5.5) | High (0.2% w/v Methyl, 0.02% w/v Ethyl) |
| DB501625.025 | High (pH 5.5) | Low (0.1% w/v Methyl, 0.01% w/v Ethyl) |
| DB501625.026 | Low (pH 4.5) | High (0.2% w/v Methyl, 0.02% w/v Ethyl) |
| DB501625.027 | Low (pH 4.5) | Low (0.1% w/v Methyl, 0.01% w/v Ethyl) |

Stability data for Formulations DB501625.024 and DB501625.026 at long term and accelerated storage conditions have been evaluated. The low paraben formulations (DB501625.025 and DB501625.027) were evaluated only for preservative efficacy. The stability data from these development stability studies are discussed below.

After 18 months storage at 25° C./60% RH, no significant changes or trends were observed in appearance, drug assay, preservative assay, pH or viscosity. A small increase in the preservatives degradation product was observed over time in the higher pH formulation (pH 5.5), but not in the low pH formulation (pH 4.5). There were differences in reporting total impurities after the first 3 months of the study. A synthetic impurity was not included in the sum of total impurities, during the first 3 months of the study. This difference in reporting explains what may appear to be a small increase in impurities after 3 months. No trend or change in the level of drug related impurities was observed throughout the study.

After 9 months storage at the accelerated storage condition (40° C./75% RH), a small drop in viscosity was observed at both pH values (4.5 and 5.5). A small upward trend in the preservative degradation product was observed only in the high pH formulation. The increase was larger than the change observed at the long term storage condition suggesting a faster degradation rate at higher temperature. No significant change or trend was observed in appearance, drug assay, preservative assay or pH after three months of storage at 40° C./75% RH.

Other than the small difference in the preservatives degradation product, no differences were observed at either condition between the two batches manufactured at the low and high ends of the target pH range. Samples stored in glass bottles at 2-8° C. did not exhibit signs of precipitation after 1 month storage at that condition.

Formulation Acceptability and Palatability

The drug product acceptability in the target patient population was a main consideration in selecting the dosage form and developing the formulation. An oral solution is suitable for pediatric or adult use across the entire anticipated dosing range. The advantage of an oral liquid preparation is that variable dose volumes can be measured and administered. With weight or age based dosing, smaller children will receive smaller dose volumes reducing the risk for incomplete ingestion and, thus, under-dosage. Efforts were made to minimize the dose volume while recognizing the need to assure accurate measurements of the dose over the anticipated range. The volume of a single dose of fenfluramine hydrochloride ranges from 0.4 mL to 6 mL. In addition, the following factors contribute to palatability and acceptability of the formulation:

Fenfluramine oral solution is an aqueous-based formulation that does not contain any oil, non-aqueous solvent or undissolved particles. Therefore, it is not expected to have texture-related issues.

The formulation is sweetened and flavored with a generally acceptable flavor (cherry). The flavor and sweetener concentrations are low to remain as close as possible to a neutral taste.

The drug substance concentration is low (2.5 mg/mL). At such low concentrations, the detectability of drug substance taste is typically low, especially with the flavoring and sweetening agents.

The formulation is slightly viscous, which typically aids in taste masking and palatability due to smaller contact area (less spread) on the tongue.

The overall acceptability and palatability of the formulation was studied in children as part of a clinical study involving the intended commercial formulation. Palatability and acceptability questions were asked in the first few months of the open-label extension (Study 1503).

Summary of Formulation Variations

Two formulation composition variations were used during clinical development. The red colored clinical composition included 1.25, 2.5 and 5 mg/mL fenfluramine hydrochloride as well as placebo. The colorless clinical compositions included the same fenfluramine hydrochloride concentrations. Table 7 presents a comparison of the two formulations used in clinical studies. A summary of the formulation variations is also discussed in this section. Table 7 lists the batches manufactured to date of each formulation and their use.

TABLE 7

Formulation Variations of Fenfluramine Hydrochloride Oral Solution Drug Product

| | Amount (mg/mL) | |
|---|---|---|
| Ingredient | Red Clinical Formulation | Colorless Clinical Formulation |
| Fenfluramine hydrochloride | Per label claim[a] | Per label claim[a] |
| Methylparaben Sodium | 2.0 | 2.0 |
| Ethylparaben Sodium | 0.2 | 0.2 |
| Sucralose | 1.0 | 1.0 |
| Hydroxyethylcellulose | 5.0 | 5.0 |
| Cherry Flavoring Powder | 0.5 | 1.0 |
| FD&C Red #40 | 0.2 | — |
| Potassium citrate monohydrate | 10.2 | 10.2 |
| Citric acid monohydrate | 3.9 | 5.5 |
| Water for irrigation | Q.S. to 1.0 mL | Q.S. to 1.0 mL |

[a]1.25 mg/mL, 2.5 mg/mL, 5 mg/mL or placebo

Example 3

Description of the Dosage Form

Fenfluramine solution for oral administration is a colorless, cherry-flavored oral solution containing 2.5 mg/mL fenfluramine hydrochloride (equivalent to 2.16 mg/mL fenfluramine) in aqueous vehicle.

The solution is contained in a multi-dose high density polyethylene (HDPE) bottle capped with child resistant, tamper-evident closures. The product will be administered using a suitable size oral syringe that will be dispensed with the drug product. A press-in bottle adapter will be inserted in the bottle opening prior to dispensing.

Composition

The composition of fenfluramine oral solution is listed in Table 8.

TABLE 8

Composition of Fenfluramine Oral Solution

| Ingredient | Function | Amount (mg/mL) |
|---|---|---|
| Fenfluramine HCl | Active | 2.5 |
| Methylparaben Sodium | Preservative | $2.0^b$ |
| Ethylparaben Sodium | Preservative | $0.2^b$ |
| Sucralose | Sweetener | 1.0 |
| Hydroxyethylcellulose | Thickener | 5.0 |
| Cherry Flavoring Powder | Flavoring agent | 1.0 |
| Potassium citrate monohydrate | Buffering agent | 10.2 |
| Citric acid monohydrate | Buffering agent | 5.5 |
| Water for irrigation | Solvent | Q.S. to 1.0 mL |

Container Closure

The primary container for fenfluramine oral solution is a white HDPE round bottle with 28 mm screw neck. Six different bottle sizes may be used to package the drug product. These are: 30, 60, 120, 250, 360 and 500 mL. All bottles are of similar design and construction.

The bottle closure is a plastic (multilayer) child-resistant cap with a tamper evident band and printed opening instructions.

The following tables present other formulations of interest.

TABLE 9

Composition of Fenfluramine Oral Solution

| Ingredient | Function | Amount (mg/mL) |
|---|---|---|
| Fenfluramine HCl | Active | 2.5 |
| Methylparaben Sodium | Preservative | $2.0^b$ |
| Ethylparaben Sodium | Preservative | $0.2^b$ |
| Sucralose | Sweetener | 1.0 |
| Xanthan gum | Thickener | 5.0 |
| Cherry Flavoring Powder | Flavoring agent | 1.0 |
| Potassium citrate monohydrate | Buffering agent | 10.2 |
| Citric acid monohydrate | Buffering agent | 5.5 |
| Water for irrigation | Solvent | Q.S. to 1.0 mL |

TABLE 10

Composition of Fenfluramine Oral Solution

| Ingredient | Function | Amount (mg/mL) |
|---|---|---|
| Fenfluramine HCl | Active | 2.5 |
| Methylparaben Sodium | Preservative | $2.0^b$ |
| Ethylparaben Sodium | Preservative | $0.2^b$ |
| Sucralose | Sweetener | 1.0 |
| Povidone K-90 | Thickener | 5.0 |
| Cherry Flavoring Powder | Flavoring agent | 1.0 |
| Potassium citrate monohydrate | Buffering agent | 10.2 |
| Citric acid monohydrate | Buffering agent | 5.5 |
| Water for irrigation | Solvent | Q.S. to 1.0 mL |

TABLE 11

Composition of Fenfluramine Oral Solution

| Ingredient | Function | Amount (mg/mL) |
|---|---|---|
| Fenfluramine HCl | Active | 2.5 |
| Methylparaben Sodium | Preservative | $2.0^b$ |
| Ethylparaben Sodium | Preservative | $0.2^b$ |
| Sucralose | Sweetener | 1.0 |
| Hydroxyethylcellulose | Thickener | 5.0 |
| Orange Flavoring Powder | Flavoring agent | 1.0 |
| Potassium citrate monohydrate | Buffering agent | 10.2 |
| Citric acid monohydrate | Buffering agent | 5.5 |
| Water for irrigation | Solvent | Q.S. to 1.0 mL |

TABLE 12

Composition of Fenfluramine Oral Solution

| Ingredient | Function | Amount (mg/mL) |
|---|---|---|
| Fenfluramine HCl | Active | 2.5 |
| Methylparaben Sodium | Preservative | $2.0^b$ |
| Ethylparaben Sodium | Preservative | $0.2^b$ |
| Sucralose | Sweetener | 1.0 |
| Hydroxyethylcellulose | Thickener | 5.0 |
| Strawberry Flavoring Powder | Flavoring agent | 1.0 |
| Potassium citrate monohydrate | Buffering agent | 10.2 |
| Citric acid monohydrate | Buffering agent | 5.5 |
| Water for irrigation | Solvent | Q.S. to 1.0 mL |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of increasing compliance with a ketogenic diet, comprising: feeding a ketogenic diet to a patient diagnosed with refractory epilepsy over a period of days; and administering to the patient over a period of days a formulation of fenfluramine hydrochloride, methylparaben sodium in a concentration of 2 mg/mL, ethylparaben sodium in a concentration of 0.2 mg/mL, sucralose in a concentration of 1.0 mg/mL, hydroxyethylcellulose in a concentration of 5.0 mg/mL, a flavoring powder in a concentration of 1.0 mg/mL, potassium citrate in a concentration of 10.2 mg/mL, citric acid monohydrate in a concentration of 5.5 mg/mL, and water; wherein the fenfluramine hydrochloride is present in the formulation in a concentration in a range of 0.5 mg/ml to 5 mg/ml.

2. The method as claimed in claim 1, wherein the refractory epilepsy is selected from the group consisting of Dravet syndrome, Lennox-Gastaut syndrome, and Doose syndrome.

3. The method of claim 1, wherein the feeding of the ketogenic diet and administration of the formulation is over a period of weeks.

4. The method as claimed in claim 3, wherein the refractory epilepsy is Dravet syndrome.

5. The method as claimed in claim 3, wherein the refractory epilepsy is Lennox-Gastaut Syndrome.

6. The method as claimed in claim 3, wherein the refractory epilepsy is Doose syndrome.

7. The method as claimed in claim 3, wherein the concentration of the fenfluramine hydrochloride is 2.5 mg/ml.

8. The method of claim 1, wherein the feeding of the ketogenic diet and administration of the formulation is over a period of months.

9. The method as claimed in claim 8, wherein the administration of the formulation is at the same time, immediately before, or immediately after each meal of the ketogenic diet, and wherein the refractory epilepsy is Dravet syndrome or Lennox-Gastaut syndrome.

10. The method as claimed in claim 1, wherein the patient is under 18 years of age.

11. The method as claimed in claim 1, wherein the flavoring powder is a cherry flavoring powder.

* * * * *